(12) United States Patent
Venkatesan et al.

(10) Patent No.: US 11,647,949 B2
(45) Date of Patent: May 16, 2023

(54) METHOD AND SYSTEM FOR STEREO-VISUAL LOCALIZATION OF OBJECT

(71) Applicant: Samsung Electronics Co., Ltd., Suwon-si (KR)

(72) Inventors: Shankar Mosur Venkatesan, Bangalore (IN); Phaneendra Kumar Yalavarthy, Bangalore (IN); Trivikram Annamalai, Bangalore (IN)

(73) Assignee: Samsung Electronics Co., Ltd., Suwon-si (KR)

( * ) Notice: Subject to any disclaimer, the term of this patent is extended or adjusted under 35 U.S.C. 154(b) by 352 days.

(21) Appl. No.: 16/620,283

(22) PCT Filed: Jun. 7, 2018

(86) PCT No.: PCT/KR2018/006486
§ 371 (c)(1),
(2) Date: Dec. 6, 2019

(87) PCT Pub. No.: WO2018/226050
PCT Pub. Date: Dec. 13, 2018

(65) Prior Publication Data
US 2020/0202517 A1    Jun. 25, 2020

(30) Foreign Application Priority Data

Jun. 7, 2017 (IN) .............................. 201741020003
Jun. 5, 2018 (IN) ............................. 2017 41020003

(51) Int. Cl.
*G06T 7/00*       (2017.01)
*A61B 5/00*      (2006.01)
(Continued)

(52) U.S. Cl.
CPC ............ *A61B 5/489* (2013.01); *G06T 7/0012* (2013.01); *G06T 7/33* (2017.01); *H04N 13/225* (2018.05);
(Continued)

(58) Field of Classification Search
CPC .......... A61B 5/489; A61B 2017/00438; A61B 2090/309; A61B 2090/371;
(Continued)

(56) References Cited

U.S. PATENT DOCUMENTS 4,249,539 A    2/1981  Vilkomerson et al.
6,108,130 A    8/2000  Raj
(Continued)

FOREIGN PATENT DOCUMENTS

JP    2004-237051 A    8/2004
JP    2009-532140 A    9/2009
(Continued)

OTHER PUBLICATIONS

Kim, Donghoon, et al. "Preliminary study for designing a novel vein-visualizing device." Sensors 17.2 (2017): 304. https://www.mdpi.com/1424-8220/17/2/304/htm (Year: 2017).*
(Continued)

*Primary Examiner* — Claire X Wang
*Assistant Examiner* — Han Hoang
(74) *Attorney, Agent, or Firm* — Jefferson IP Law, LLP

(57) ABSTRACT

Embodiments herein provide a method for stereo-visual localization of an object by a stereo-visual localization apparatus. The method includes generating, by a stereo-visual localization apparatus, a stereo-visual interface displaying the first stereo image of the object and the first stereo image of the subject in a first portion and the second stereo image of the object and the second stereo image of the subject in a second portion. Further, the method includes
(Continued)

detecting, by the stereo-visual localization apparatus, a movement of the subject to align the subject in the field of view with the object. Furthermore, the method includes visually aligning, by the stereo-visual localization apparatus, the subject with the object based on the movement by simultaneously changing apparent position of the first and the second stereo images of the subject in each of the first portion and the second portion in the stereo-visual interface.

12 Claims, 21 Drawing Sheets

(51) Int. Cl.
  *G06T 7/33* (2017.01)
  *H04N 13/279* (2018.01)
  *H04N 13/225* (2018.01)
  *G02B 30/00* (2020.01)

(52) U.S. Cl.
  CPC ............ *H04N 13/279* (2018.05); *G02B 30/00* (2020.01); *G06T 2207/10021* (2013.01); *G06T 2207/10132* (2013.01); *G06T 2207/30101* (2013.01)

(58) Field of Classification Search
  CPC ........ A61B 2090/372; A61B 2090/378; A61B 90/36; A61B 2090/364; A61B 2090/502; A61B 5/00; A61B 5/0059; G06T 7/0012; G06T 7/33; G06T 2207/10021; G06T 2207/10132; G06T 2207/30101; H04N 13/225; H04N 13/279; H04N 2013/0081; H04N 13/239; H04N 2213/001; G02B 30/00
  See application file for complete search history.

(56) References Cited

U.S. PATENT DOCUMENTS

| | | | |
|---|---|---|---|
| 8,670,816 | B2 | 3/2014 | Green et al. |
| 2010/0177182 | A1 | 7/2010 | Kagenow et al. |
| 2011/0092811 | A1* | 4/2011 | Yasui .................... A61B 5/489 600/424 |
| 2013/0271363 | A1 | 10/2013 | Poznansky et al. |
| 2014/0046291 | A1* | 2/2014 | Harris ............... A61M 5/16836 604/503 |
| 2016/0256101 | A1 | 9/2016 | Aharoni et al. |
| 2020/0008899 | A1* | 1/2020 | Tripathi ................. G02B 21/22 |

FOREIGN PATENT DOCUMENTS

| | | |
|---|---|---|
| JP | 2010-148853 A | 7/2010 |
| KR | 10-2013-0028534 A | 3/2013 |
| WO | 2015/031481 A1 | 3/2015 |

OTHER PUBLICATIONS

Kim, Mingyu, Changyu Jeon, and Jinmo Kim. "A study on immersion and presence of a portable hand haptic system for immersive virtual reality." Sensors 17.5 (2017): 1141. https://www.mdpi.com/1424-8220/17/5/1141 (Year: 2017).*

Annamalai et al.; Low Cost Vein Detector; Design Degree Show 2015; Heatlh and Well Being; Jun. 13-17, 2015; ddsidc.com/2015/?portfolio=low-cost-vein-detector.

JM; Vein Viewer Finder 3D Headset Portable Hands-Free Vascular Imaging Visualization Glass Type optical head-mounted display; Nov. 22, 2019; https://www.amazon.com/Viewer-Finder-Headset-Visualization-head-mounted/dp/B06Y4919X4.

Sorrel; Thimble: A Bluetooth Braille Smart-Finger; WIRED; Gear; Dec. 27, 2010; https://www.wired.com/2010/12/thimble-a-bluetooth-braille-smart-finger/.

Chen et al.; Portable robot for autonomous venipuncture using 3D near infrared image guidance; HHS Public Access; Author manuscript Technology (Singap World Sci). Author manuscript; available in PMC Jun. 26, 2015; Sep. 2013; Piscataway, NJ.

Yalavarthy et al.; Integrable Vein Viewing System in Hand Held Devices; 2009; India.

Ganesh; Depth and Size Limits for the Visibility of Veins Using the VeinViewer Imaging System; University of Tennessee Health Science Center UTHSC Digital Commons; Theses and Dissertations (ETD); College of Graduate Health Sciences; May 2007.

Accuvein; AV400 Vein Viewing System; Nov. 22, 2019; www.accuvein.com/products/catalog/av400-vein-viewing-system/.

Indian Office Action dated Mar. 15, 2021; Indian Appln. No. 201741020003.

* cited by examiner

[Fig. 1]
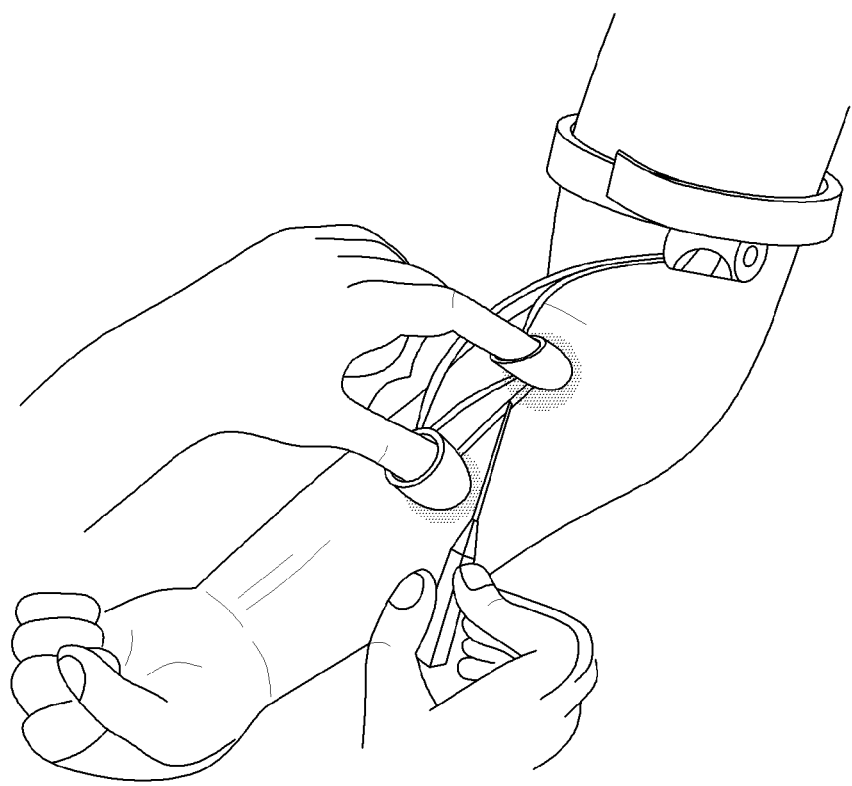

[Fig. 2a]
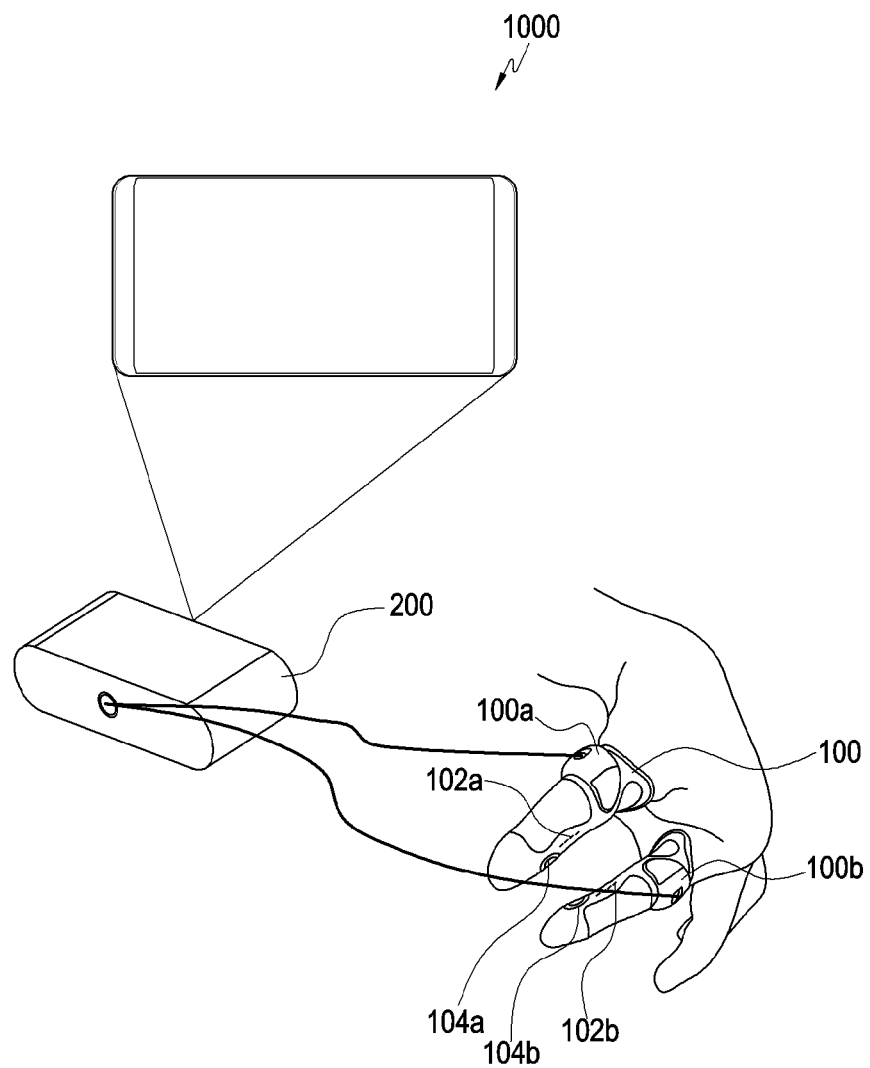

[Fig. 2b]
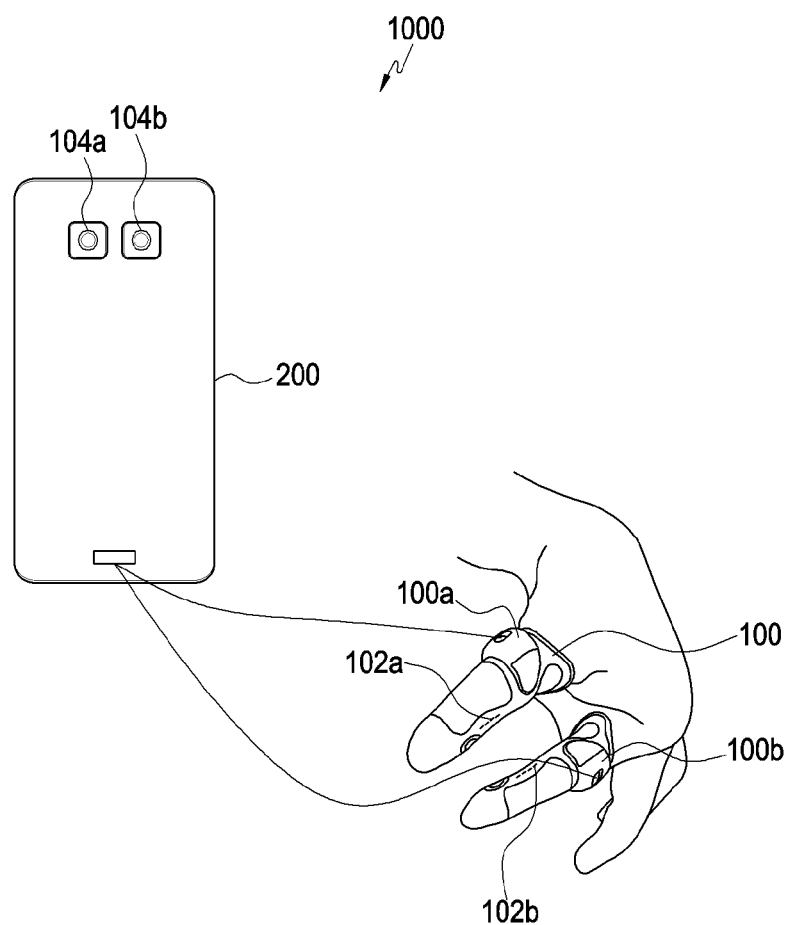

[Fig. 2c]
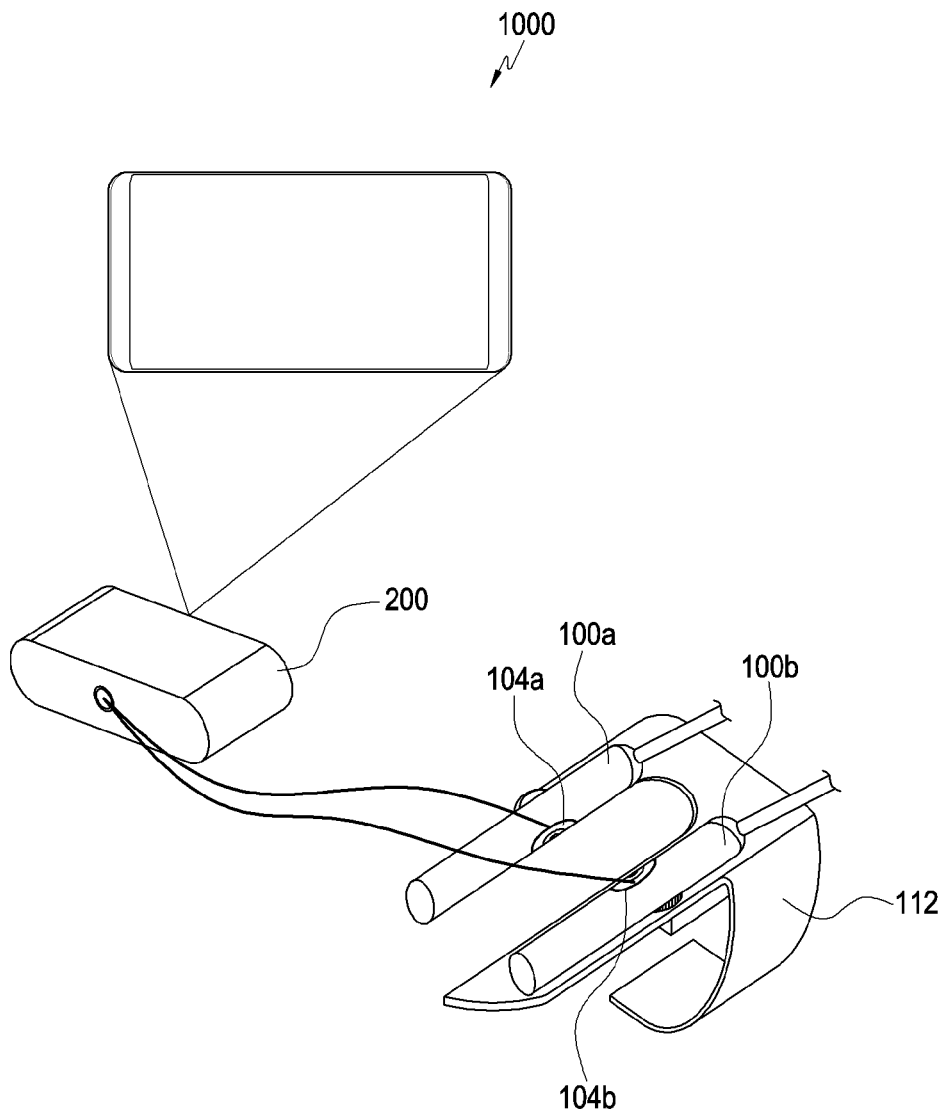
[Fig. 3a]
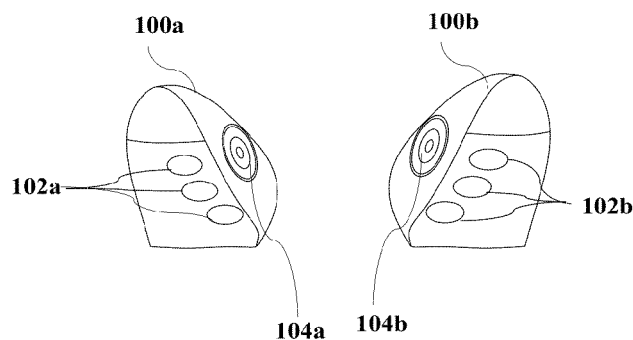

[Fig. 3b]
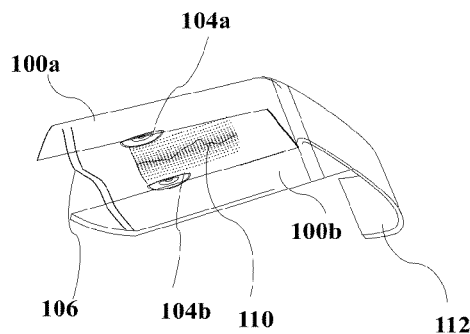
[Fig. 3c]
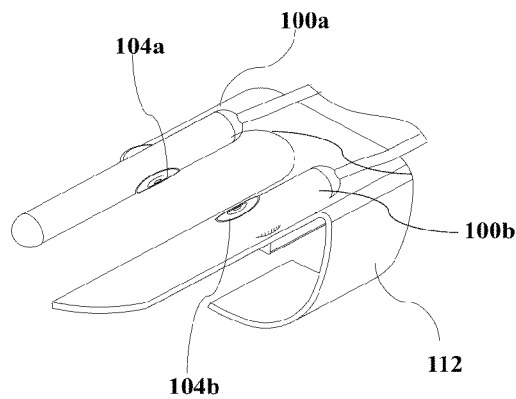
[Fig. 4a]
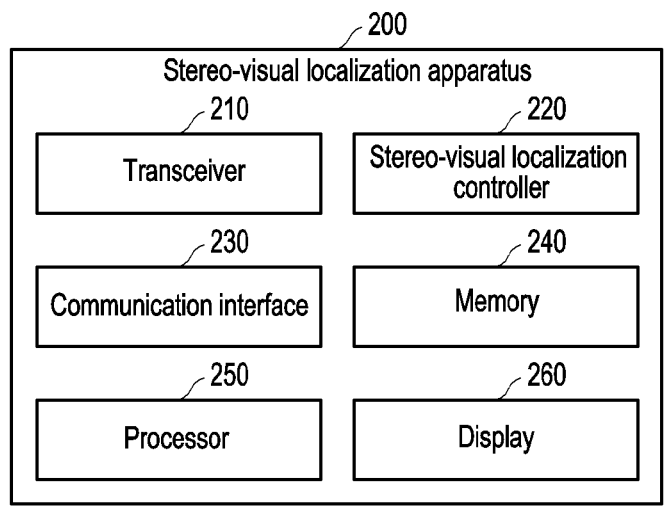

[Fig. 4b]
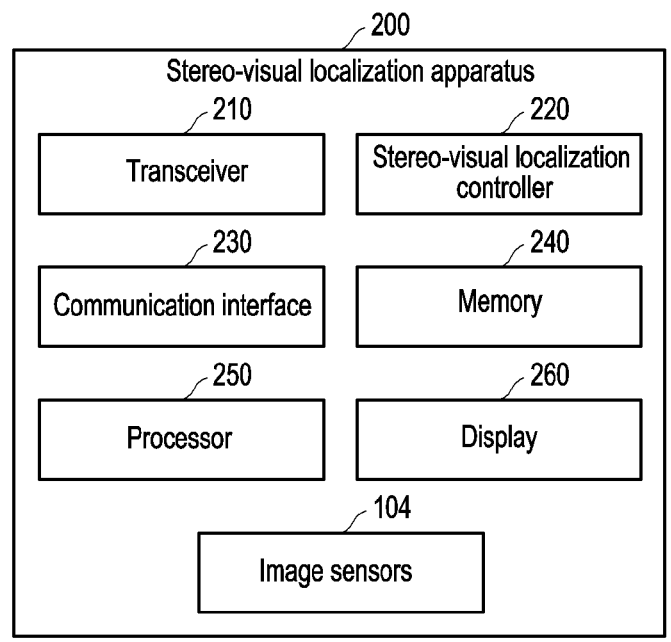
[Fig. 5]
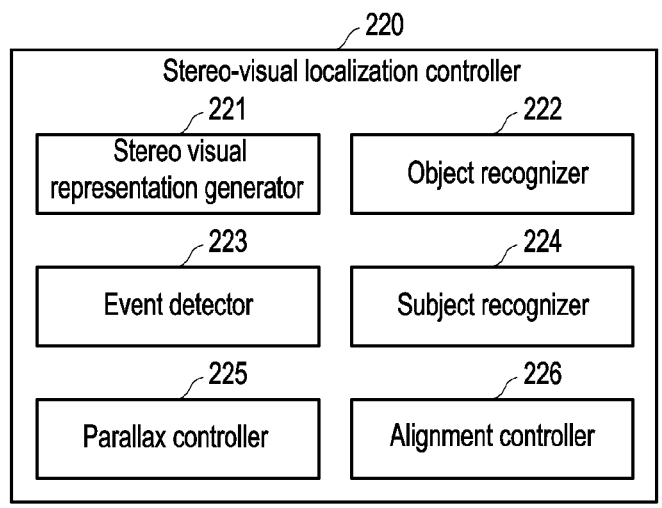

[Fig. 6]
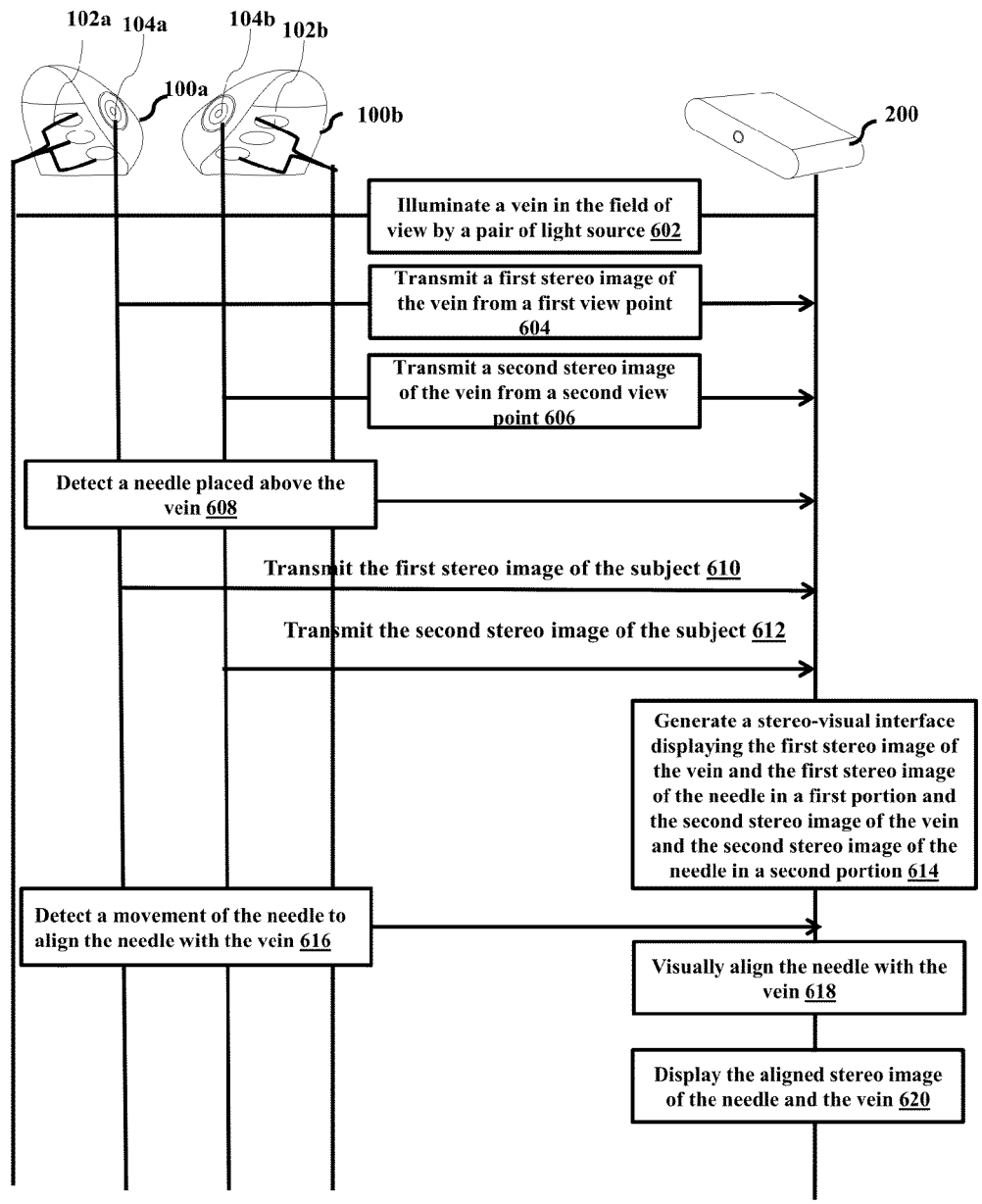

[Fig. 7a]
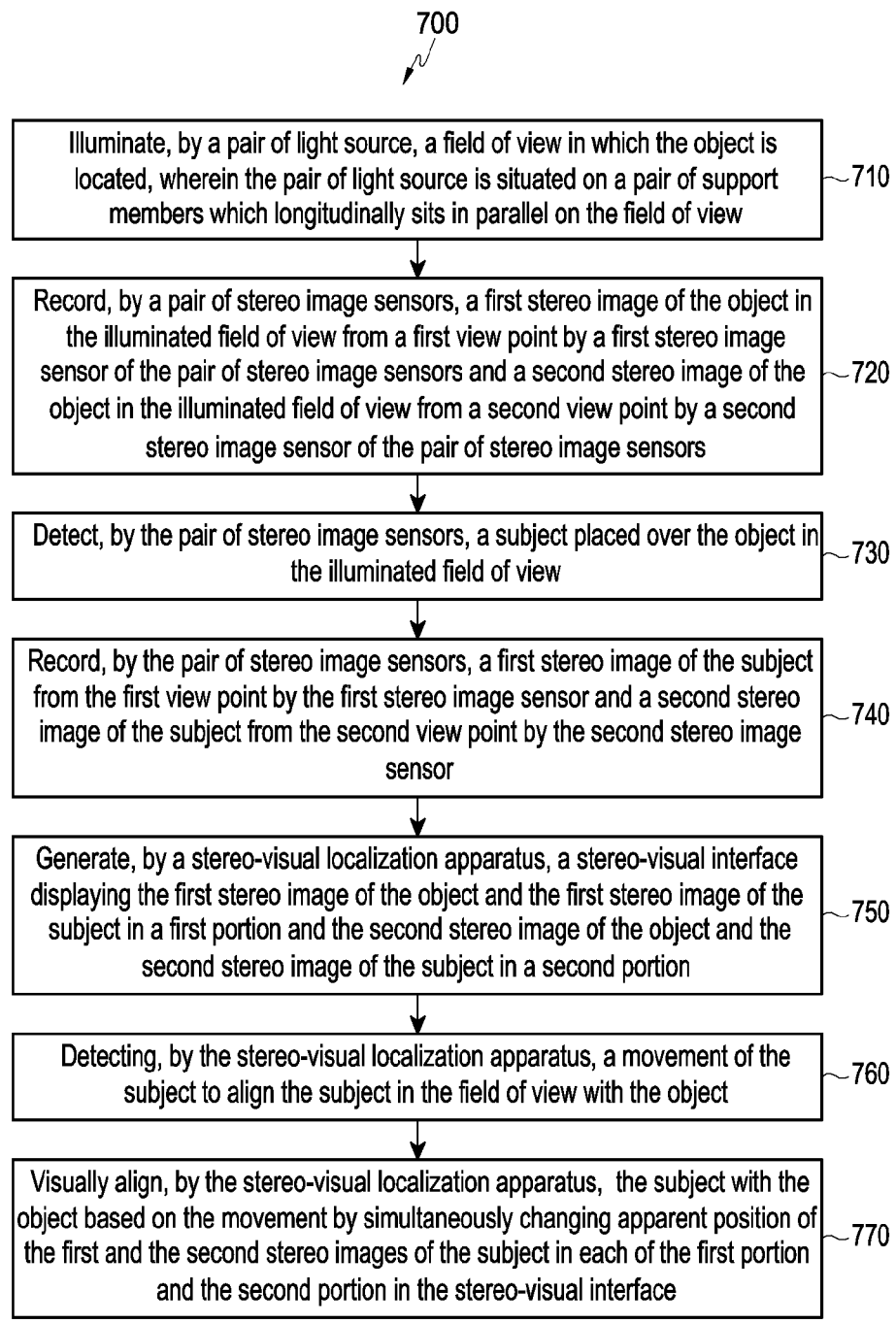

[Fig. 7b]
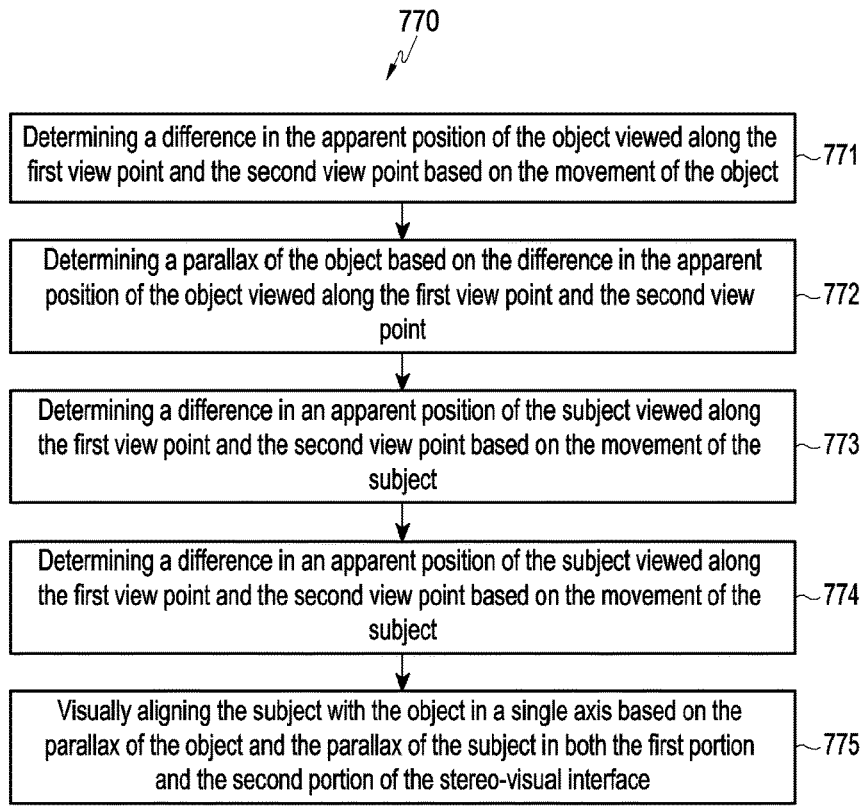
[Fig. 8a]
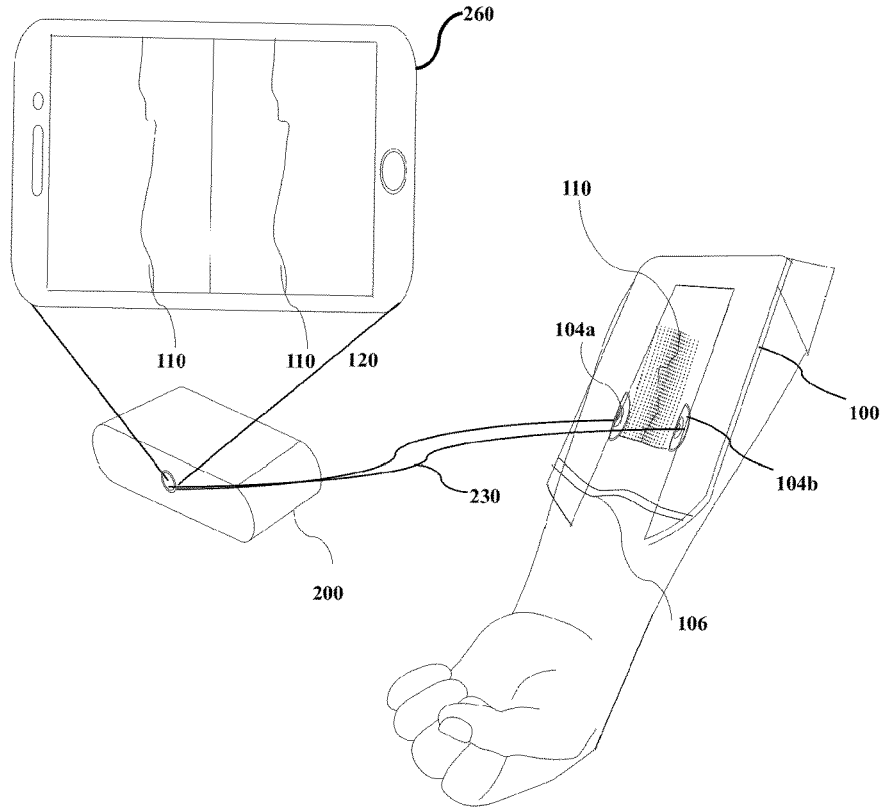

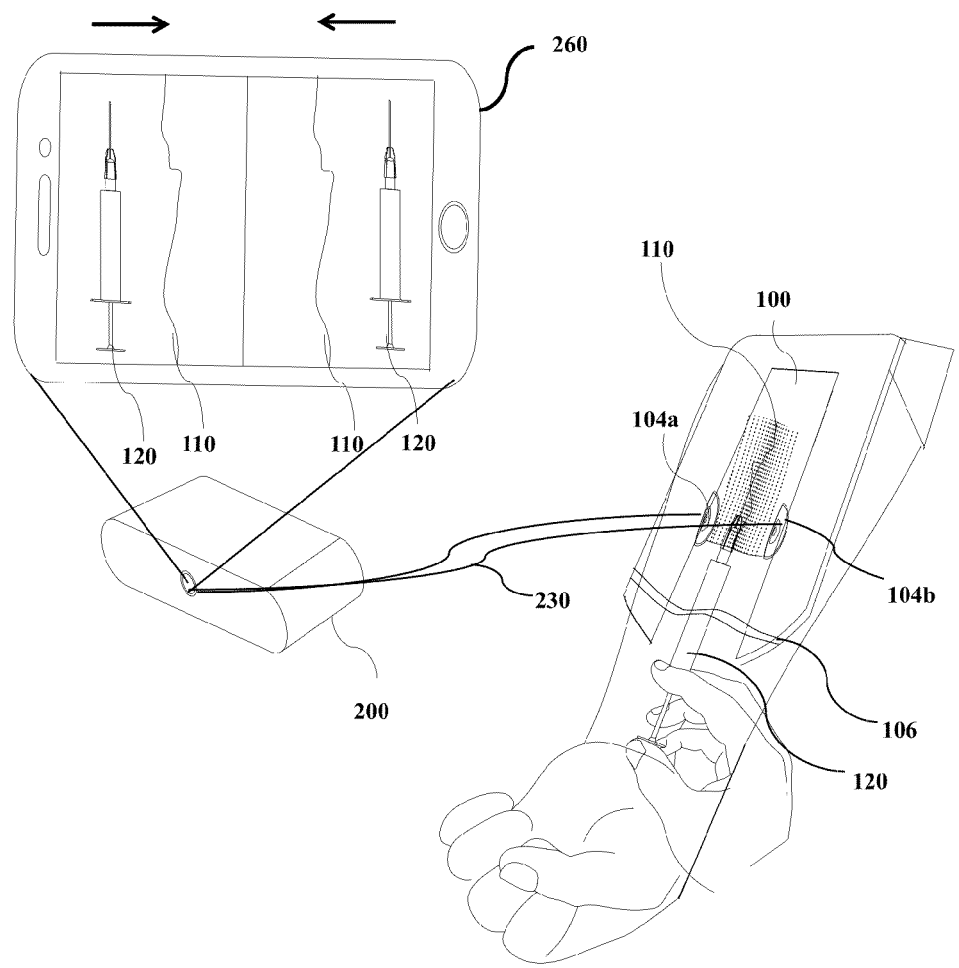

[Fig. 8c]
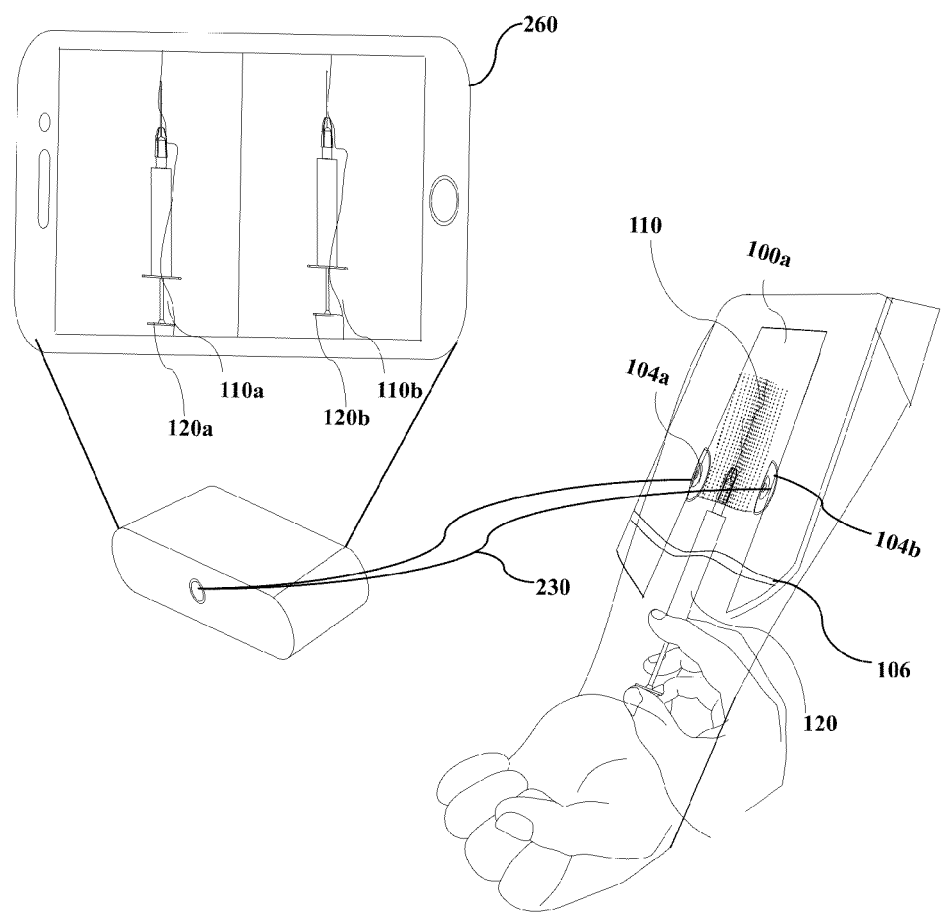

[Fig. 9a]
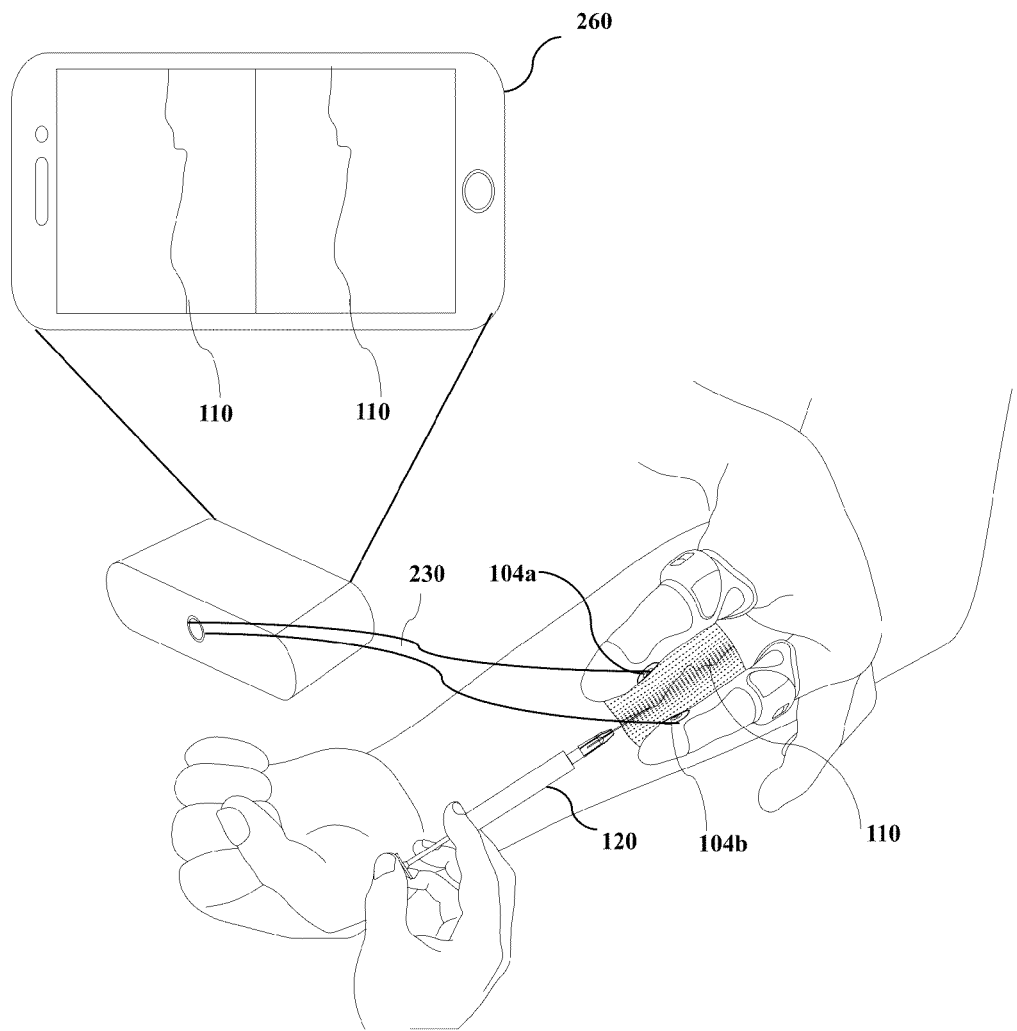

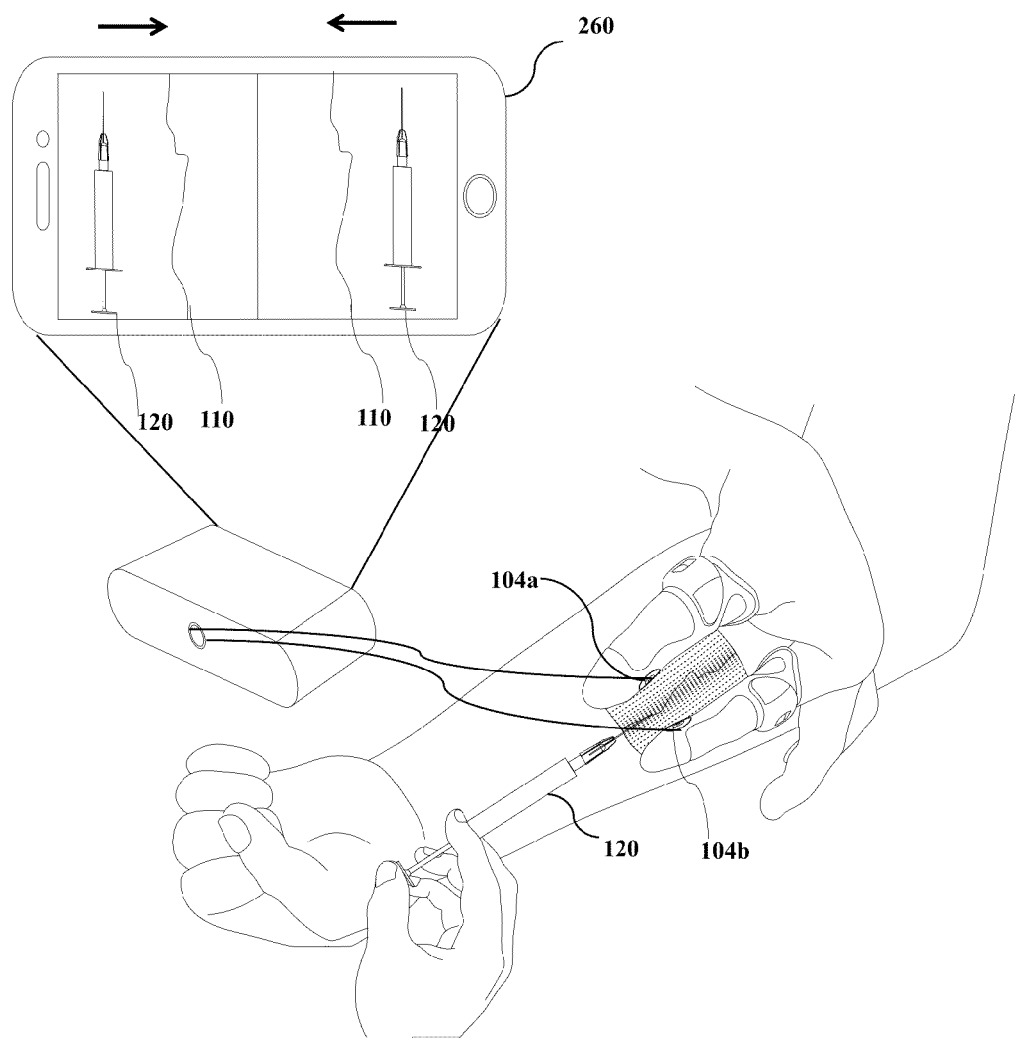
[Fig. 9b]

[Fig. 9c]
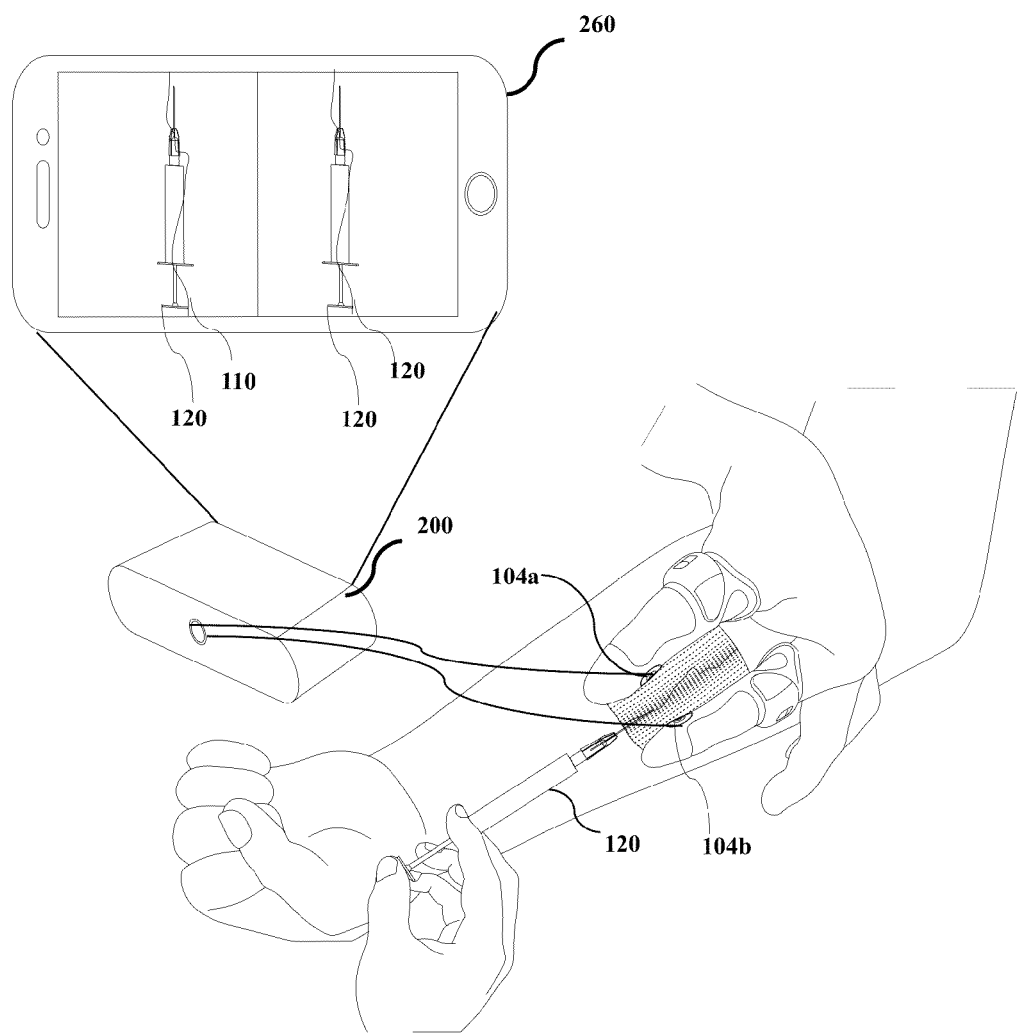

[Fig. 10a]
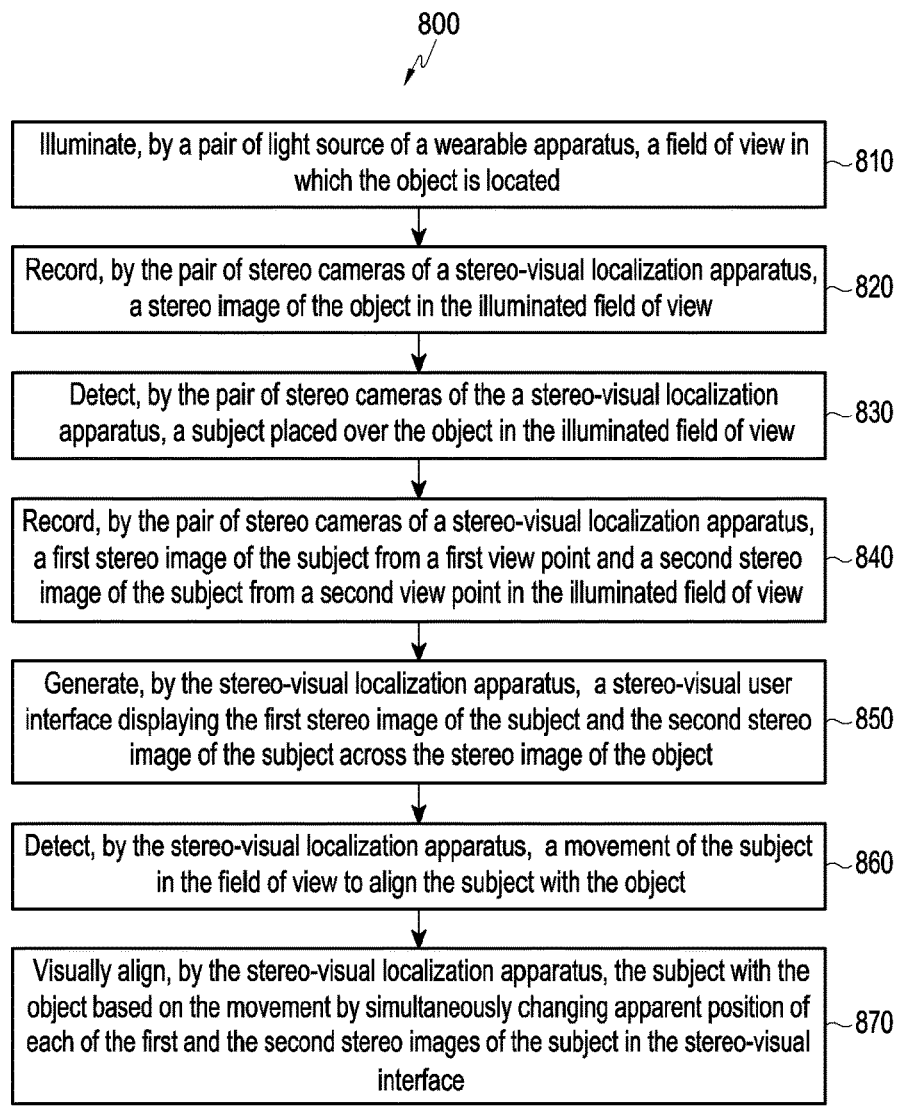
[Fig. 10b]
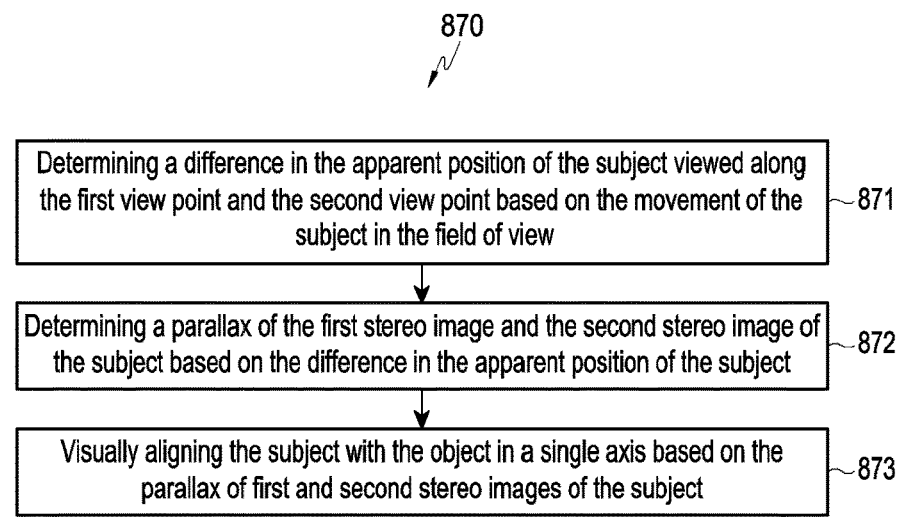

[Fig. 11a]
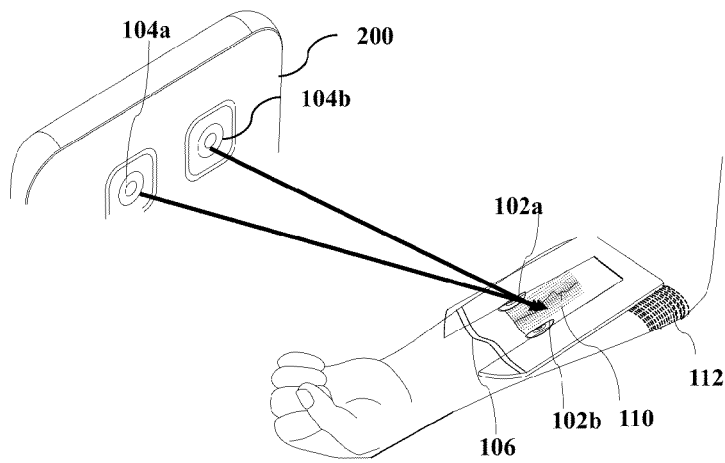
[Fig. 11b]
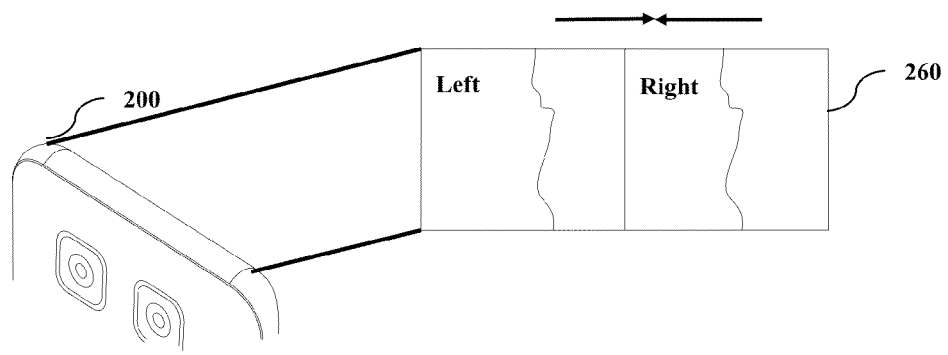
[Fig. 11c]
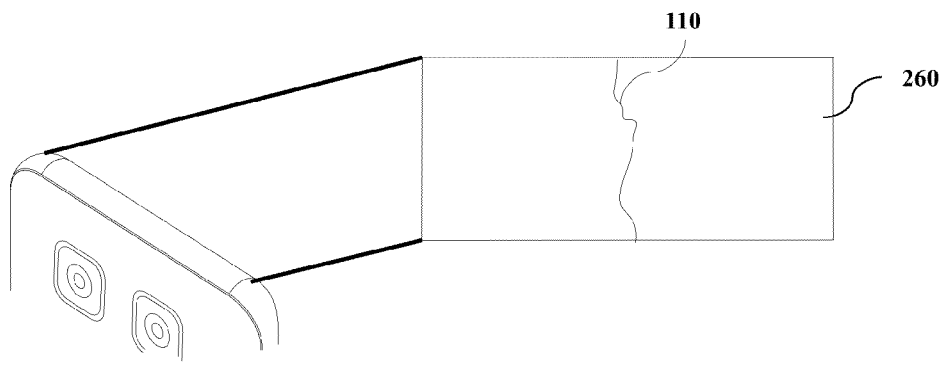

[Fig. 11d]
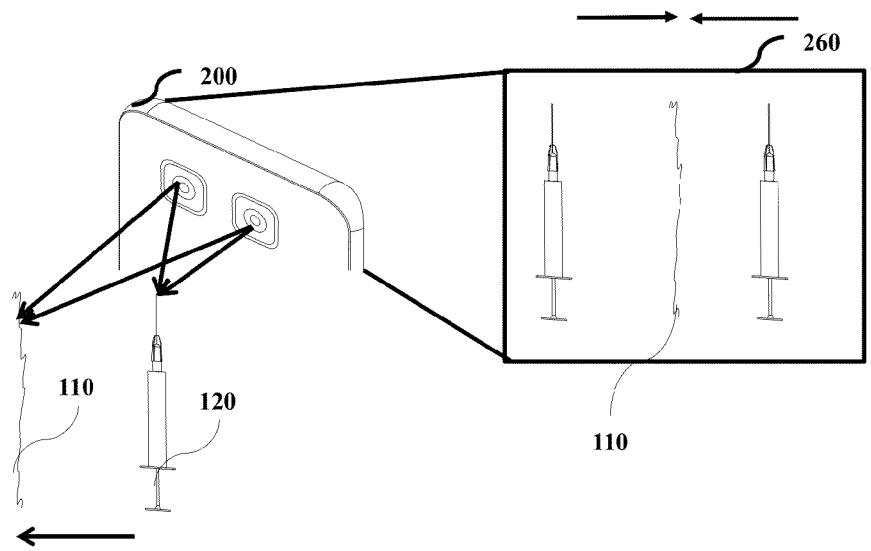
[Fig. 11e]
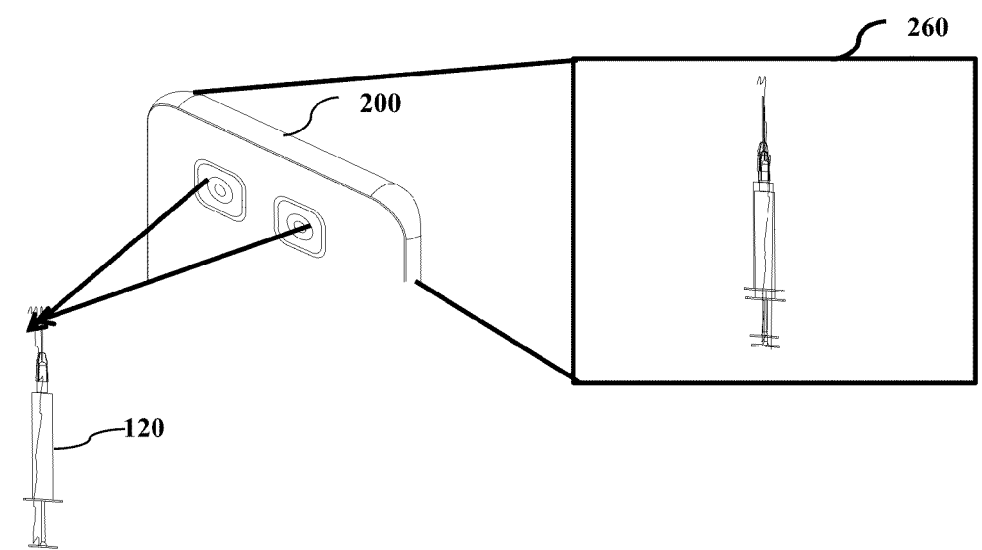
[Fig. 12a]
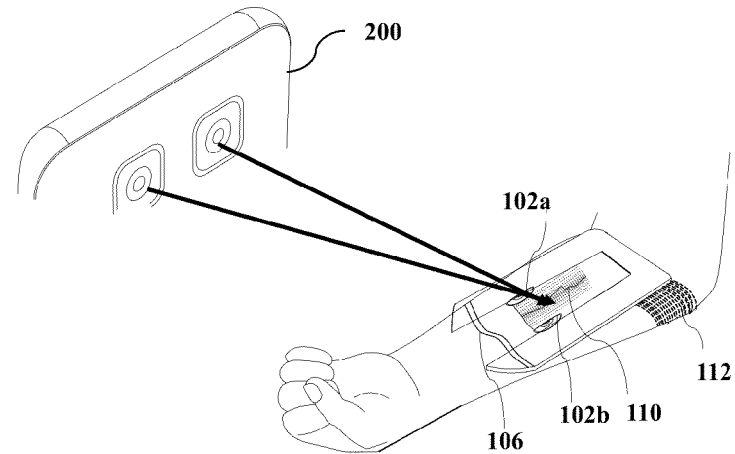

[Fig. 12b]
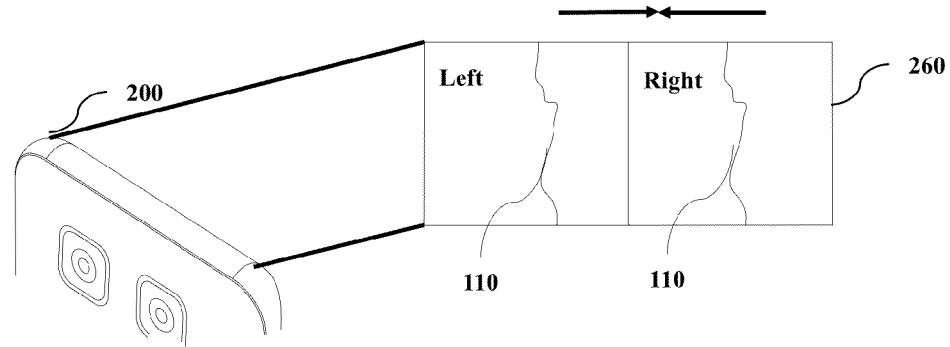
[Fig. 12c]
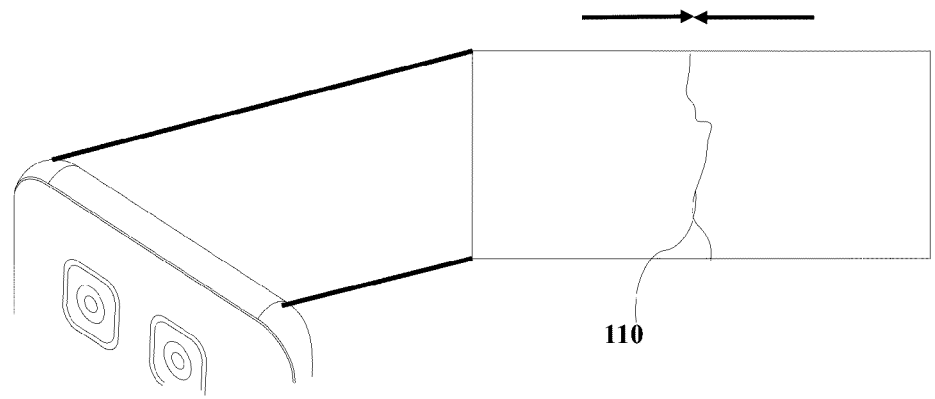
[Fig. 12d]
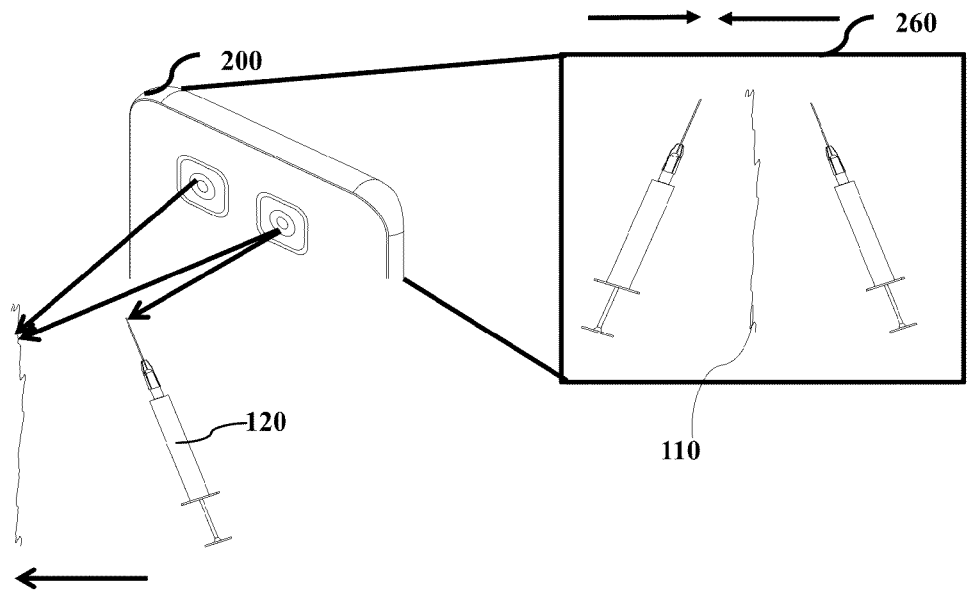

[Fig. 12e]
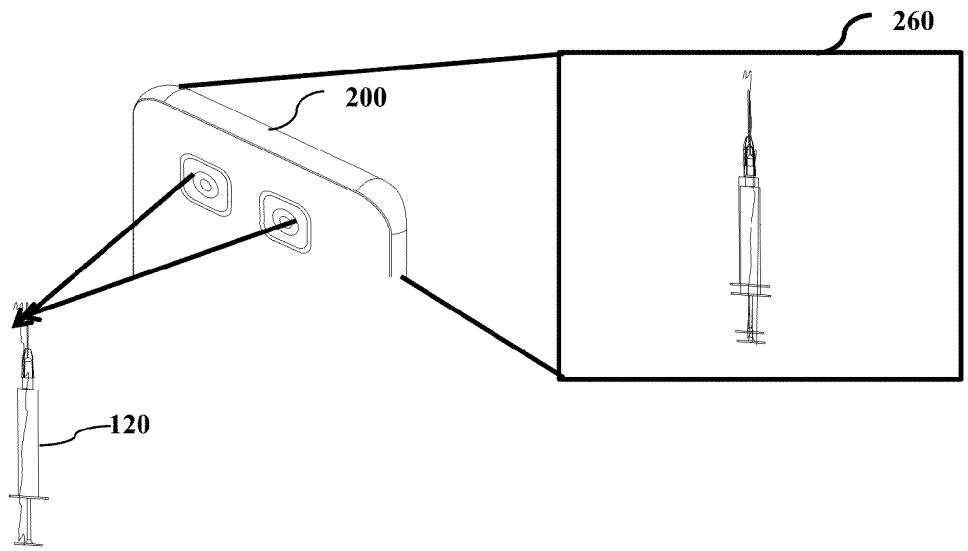
[Fig. 13]
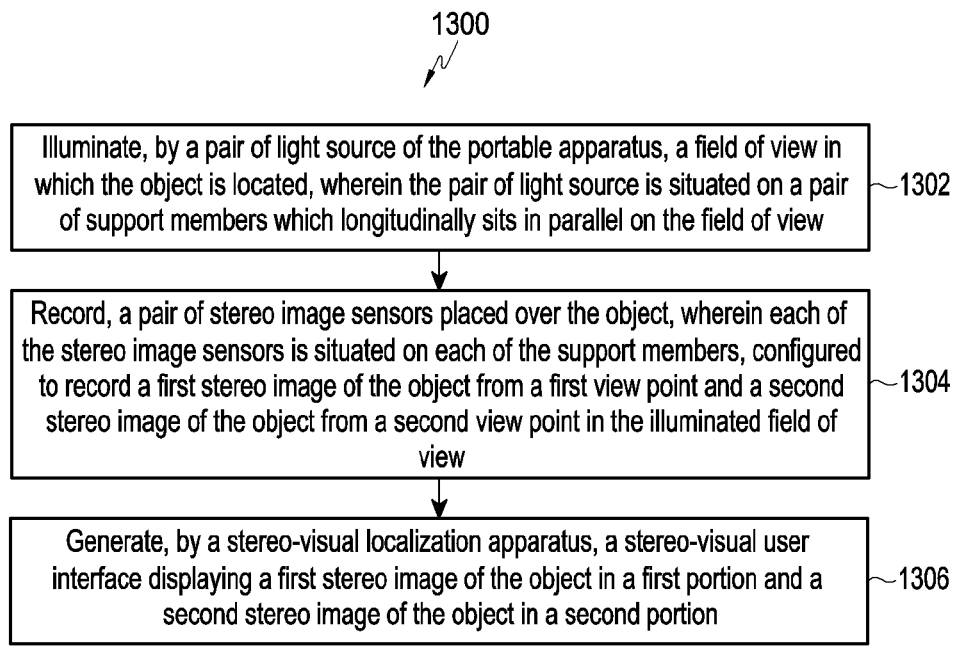

[Fig. 14a]
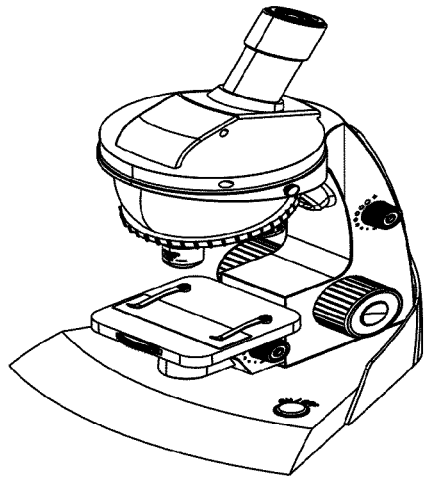
[Fig. 14b]
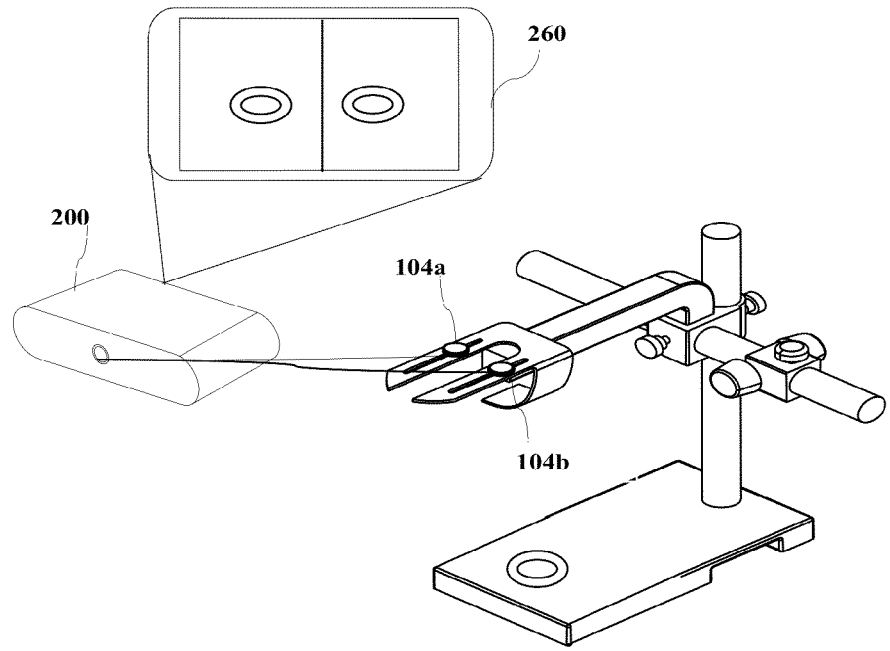
[Fig. 15a]
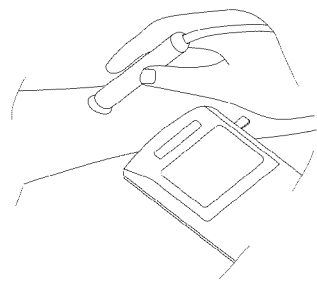

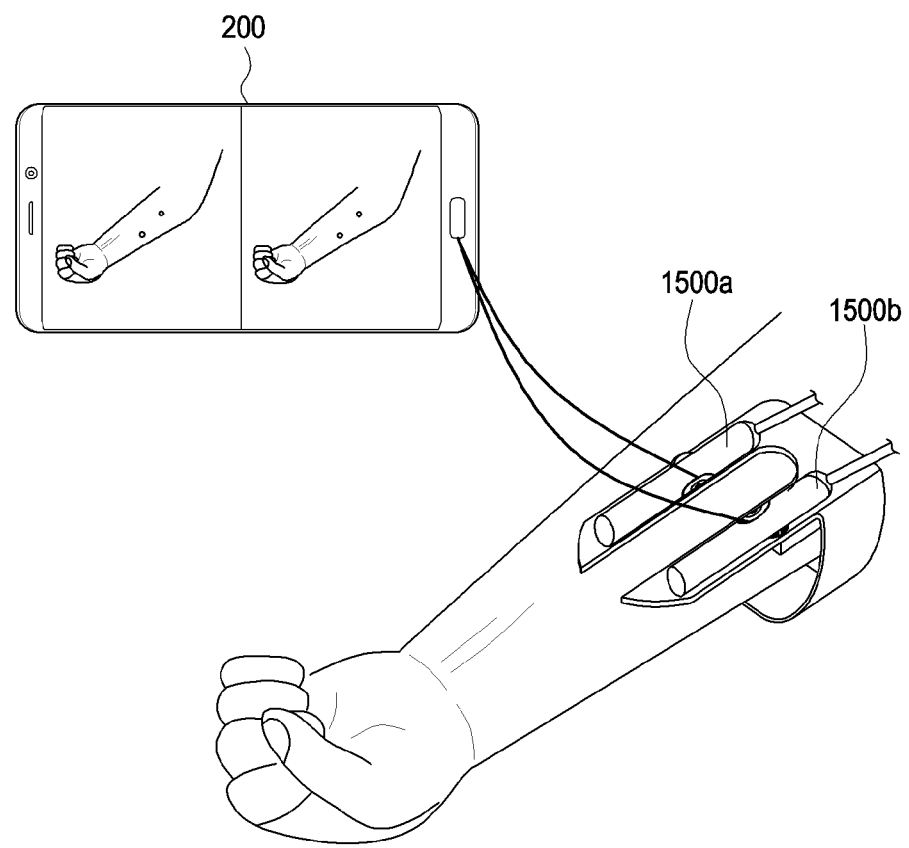
[Fig. 15b]

ically localize the blood vessel without any errors, a discomfort to the patient, or the like. Many times locating the blood vessel (e.g., a vein or artery) is a challenge, especially in young, elderly, dark-skinned, and obese patients whose veins are small, fragile, rolling, or obscured by melanin or subcutaneous fat. Hence, this results in a very difficult task of spotting the vein in a single attempt. Further, a clinician/phlebotomist performs multiple attempts of a needle insertion to find the blood vessel beneath a patient's skin due to an inexperience of the clinician/phlebotomist and/or difficulty in locating the blood vessel. This results in several undesirable complications such as a pain, mistake in multiple punctures, a patient discomfort, a therapy delay, or the like.

METHOD AND SYSTEM FOR STEREO-VISUAL LOCALIZATION OF OBJECT

CROSS-REFERENCE TO RELATED APPLICATION(S) AND CLAIM OF PRIORITY

This application is a National Phase Entry of PCT International Application No. PCT/KR2018/006486, which was filed on Jun. 7, 2018 and claims priority under 35 U.S.C. § 119 of an Indian patent application number 201741020003, filed on Jun. 7, 2017, in the Indian Patent Office, and of an Indian patent application number 201741020003, filed on Jun. 5, 2018, in the Indian Patent Office, the disclosure of which is incorporated herein by reference in its entirety.

TECHNICAL FIELD

The present disclosure relates to a portable localization device, and more particularly relates to a method and system for stereo-visual localization of an object using the portable localization device.

BACKGROUND ART

Generally, several medical procedures require a puncture of subcutaneous blood vessels of a patient to obtain a blood from the patient. Hence, it is necessary to precisely localize the blood vessel without any errors, a discomfort to the patient, or the like. Many times locating the blood vessel (e.g., a vein or artery) is a challenge, especially in young, elderly, dark-skinned, and obese patients whose veins are small, fragile, rolling, or obscured by melanin or subcutaneous fat. Hence, this results in a very difficult task of spotting the vein in a single attempt. Further, a clinician/phlebotomist performs multiple attempts of a needle insertion to find the blood vessel beneath a patient's skin due to an inexperience of the clinician/phlebotomist and/or difficulty in locating the blood vessel. This results in several undesirable complications such as a pain, mistake in multiple punctures, a patient discomfort, a therapy delay, or the like.

There are lot of vein image enhancers using an image re-projection technology to locate the vein in a captured image. However, the cost of the vein image enhancers is too exorbitant to be afforded by small scale healthcare centers. In an existing method, a stereo-camera based robotic vein finding in a Three-Dimensional (3D) image is disclosed. Further, a depth information is determined using a Near Infrared Light (NIR), a needle tracking, and a needle insertion is disclosed. However, there exists a difficulty in reconstruction of the 3D image based on stereo-image disparity and results in a high expensive vein-finding system.

In another existing method entitled to "low cost vein detector" as shown in FIG. 1, describes about a device helps to visualize the veins and perform the vein-puncture process with ease. The device includes an array of LEDs placed inside thimbles, where the clinician uses the thimbles to visualize the vein accurately. However, they may cause an error in finding the vein accurately, as the depth information of the vein is not properly determined.

In another existing method, a smartphone equipped with a camera under the NIR and Visible Range (VIS) condition, is used for finding the vein of a user. This method is less expensive, however the camera does not provide the depth information of the vein and the method cannot be reliably adapted for venipuncture. Further, in yet another existing method, the smartphone equipped with a high quality stereo-camera is used for finding the vein. However, the cost of the high quality stereo-camera is expensive.

DISCLOSURE OF INVENTION

Technical Problem

Thus, it is desired to address the above mentioned disadvantages or other shortcomings or at least provide a useful alternative.

Solution to Problem

The principal object of the embodiments herein is to provide a method and system for stereo-visual localization of an object.

Another object of the embodiments herein is to record a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors.

Another object of the embodiments herein is to detect a subject placed over the object in the illuminated field of view.

Another object of the embodiments herein is to record a first stereo image of the subject from the first view point by the first stereo image sensor and a second stereo image of the subject from the second view point by the second stereo image sensor.

Another object of the embodiments herein is to generate a stereo-visual interface displaying the first stereo image of the object and the first stereo image of the subject in a first portion and the second stereo image of the object and the second stereo image of the subject in a second portion.

Another object of the embodiments herein is to detect a movement of the subject to align the subject in the field of view with the object.

Another object of the embodiments herein is to visually align the subject with the object based on the movement by simultaneously changing apparent position of the first and the second stereo images of the subject in each of the first portion and the second portion in the stereo-visual interface.

Another object of the embodiments herein is to determine a difference in the apparent position of the object viewed along the first view point and the second view point based on the movement of the object.

Another object of the embodiments herein is to determine a parallax of the object based on the difference in the apparent position of the object viewed along the first view point and the second view point.

Another object of the embodiments herein is to determine a difference in an apparent position of the subject viewed along the first view point and the second view point based on the movement of the subject.

Another object of the embodiments herein is to determine a parallax of the subject based on the difference in the apparent position of the subject viewed along the first view point and the second view point.

Another object of the embodiments herein is to visually align the subject with the object in a single axis based on the parallax of the object and the parallax of the subject in both the first portion and the second portion of the stereo-visual interface.

Another object of the embodiments herein is to determine pixels corresponding to the object in the first image and pixels corresponding to the object in the second image.

Another object of the embodiments herein is to record the stereo image of the object by combining the pixels corresponding to the object in the first image with the pixels corresponding to the object in the second image.

Accordingly the embodiments herein provide a system for stereo-visual localization of an object. The system includes a portable apparatus operably coupled with a stereo-visual localization apparatus. The portable apparatus includes a pair of support members which longitudinally sits in parallel on a field of view in which the object is located. Further, the portable apparatus includes pair of light source, each of which is situated on each of the support members, configured to illuminate the field of view in which the object is located. Further, the portable apparatus includes a pair of stereo image sensors placed over the object, each of the stereo image sensors is situated on each of the support members. The pair of stereo image sensors are configured to record a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors.

In an embodiment, the pair of stereo image sensors are further configured to detect a subject placed over the object in the illuminated field of view. Further, the pair of stereo image sensors are configured to record a first stereo image of the subject from the first view point by the first stereo image sensor and a second stereo image of the subject from the second view point by the second stereo image sensor. Further, the pair of stereo image sensors are configured to transmit the first stereo image of the subject from the first view point and the second stereo image of the subject from the second view point to a stereo-visual localization apparatus for stereo localization of object.

In an embodiment, the stereo-visual localization apparatus is configured to receive the first stereo image of the subject from the first view point and the second stereo image of the subject from the second view point from the portable apparatus. Further, the stereo-visual localization apparatus generates a stereo-visual interface displaying the first stereo image of the object and the first stereo image of the subject in a first portion and the second stereo image of the object and the second stereo image of the subject in a second portion. Further, the stereo-visual localization apparatus detects a movement of the subject to align the subject in the field of view with the object. Further, the stereo-visual localization apparatus visually aligns the subject with the object based on the movement by simultaneously changing apparent position of the first and the second stereo images of the subject in each of the first portion and the second portion in the stereo-visual interface.

In an embodiment, visually align the subject with the object based on the movement by simultaneously changing apparent position of the first and the second stereo images of the subject in each of the first portion and the second portion in the stereo-visual representation includes determine a difference in the apparent position of the object viewed along the first view point and the second view point based on the movement of the object. Further, visually align the subject with the object includes determine a parallax of the object based on the difference in the apparent position of the object viewed along the first view point and the second view point. Further, visually align the subject with the object includes determine a difference in an apparent position of the subject viewed along the first view point and the second view point based on the movement of the subject. Further, visually align the subject with the object includes determine a parallax of the subject based on the difference in the apparent position of the subject viewed along the first view point and the second view point. Furthermore, visually align the subject with the object in a single axis based on the parallax of the object and the parallax of the subject in both the first portion and the second portion of the stereo-visual interface.

In an embodiment, the parallax of the object and the parallax of the subject is zero when the object and the subject are in the single axis.

In an embodiment, the portable apparatus further includes a fastening band to fasten the portable apparatus, and a supporting member to provide a support to a subject, in which the supporting member includes a notch-depression for resting the subject to align with the object.

In an embodiment, the object is a buried structure beneath a user skin and the subject is a needle.

In an embodiment, the first stereo image of the subject appears on a left side of the first stereo image of the object in the first portion of the stereo-visual user interface, and the second stereo image of the subject appears on a right side of the second stereo image of the object in the second portion of the stereo-visual user interface.

Accordingly the embodiments herein provide a system for stereo-visual localization of an object. The system includes a portable apparatus operably coupled with a stereo-visual localization apparatus. The portable apparatus includes a pair of support members which longitudinally sits in parallel on a field of view in which the object is located. Further, the portable apparatus includes pair of light source, each of which is situated on each of the support members, configured to illuminate the field of view in which the object is located. Further, the stereo-visual localization apparatus includes a pair of stereo image sensors proximity to the portable device and the object. The pair of stereo image sensors are configured to record a stereo image of the object in the illuminated field of view. Further, the pair of stereo image sensors are configured to detect a subject placed over the object in the illuminated field of view. Further, the pair of stereo image sensors are configured to record a first stereo image of the subject from a first view point and a second stereo image of the subject from a second view point in the illuminated field of view.

Further, the stereo-visual localization apparatus includes the stereo-visual localization controller configured to generate a stereo-visual user interface displaying the first stereo image of the subject and the second stereo image of the subject across the stereo image of the object. The stereo-visual localization controller is configured to detect a movement of the subject in the field of view to align the subject with the object. Further, the stereo-visual localization controller is configured to visually align the subject with the object based on the movement by simultaneously changing apparent position of each of the first and the second stereo images of the subject in the stereo-visual interface.

In an embodiment, visually align the subject with the object based on the movement by simultaneously changing apparent position of each of the first and the second stereo images of the subject of the subject in the stereo-visual representation includes determine a difference in the apparent position of the subject viewed along the first view point and the second view point based on the movement of the subject in the field of view, determine a parallax of the first stereo image and the second stereo image of the subject based on the difference in the apparent position of the subject, and visually align the subject with the object in a single axis based on the parallax of first and second stereo images of the subject.

In an embodiment, the parallax of the first and second stereo images of the subject is zero when the object and the subject are in the single axis.

In an embodiment, record the stereo image of the object in the illuminated field of view includes capture a first image of the object from a first view point and a second image of the object from a second view point in the illuminated field of view, determine pixels corresponding to the object in the first image and pixels corresponding to the object in the second image and record the stereo image of the object by combining the pixels corresponding to the object in the first image with the pixels corresponding to the object in the second image.

Accordingly the embodiments herein provide a system for stereo-visual localization of an object. The system includes a portable apparatus operably coupled with a stereo-visual localization apparatus. The portable apparatus includes a pair of support members which longitudinally sits in parallel on a field of view in which the object is located. Further, the portable apparatus includes pair of light source, each of which is situated on each of the support members, configured to illuminate the field of view in which the object is located. Further, the portable apparatus includes a pair of stereo image sensors placed over the object, in which each of the stereo image sensors is situated on each of the support members. The pair of stereo image sensors are configured to record a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors. Furthermore, the stereo-visual localization apparatus is configured to generate a stereo-visual user interface displaying the first stereo image of the object in a first portion and the second stereo image of the object in a second portion.

In an embodiment, the image sensors is one of a stereo-camera device and an ultrasound device.

Accordingly the embodiments herein provide a portable apparatus for stereo-visual localization of an object. The portable apparatus includes a pair of support members which longitudinally sits in parallel on a field of view in which the object is located. Further, the portable apparatus includes a pair of light source, each of which is situated on each of the support members, configured to illuminate the field of view in which the object is located. Further, the portable apparatus includes a pair of stereo image sensors placed over the object, each of the stereo image sensors is situated on each of the support members. The pair of stereo image sensors are configured to record a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors. Further, the pair of stereo image sensors are configured to detect a subject placed over the object in the illuminated field of view. Further, the pair of stereo image sensors are configured to record a first stereo image of the subject from the first view point by the first stereo image sensor and a second stereo image of the subject from the second view point by the second stereo image sensor. Further, the pair of stereo image sensors are configured to transmit the first stereo image of the subject from the first view point and the second stereo image of the subject from the second view point to a stereo-visual localization apparatus for stereo-visual localization of the object.

Accordingly the embodiments herein provide a stereo-visual localization apparatus for stereo-visual localization of an object. The stereo-visual localization apparatus includes a memory, a processor; and a stereo-visual alignment controller, operationally communicate with a portable apparatus. The stereo-visual alignment controller is configured to receive the first stereo image of the subject from the first view point and the second stereo image of the subject from the second view point from the portable apparatus. Further, the stereo-visual alignment controller is configured to generate a stereo-visual interface displaying the first stereo image of the object and the first stereo image of the subject in a first portion and the second stereo image of the object and the second stereo image of the subject in a second portion. Further, the stereo-visual alignment controller is configured to detect a movement of the subject to align the subject in the field of view with the object. Furthermore, the stereo-visual alignment controller is configured to visually align the subject with the object based on the movement by simultaneously changing apparent position of the first and the second stereo images of the subject in each of the first portion and the second portion in the stereo-visual interface.

Accordingly the embodiments herein provide a stereo-visual localization apparatus for stereo-visual localization of an object. The stereo-visual localization apparatus includes a memory, a processor, and a pair of stereo image sensors, proximity to a portable device and the object, configured to record a stereo image of the object in an illuminated field of view. Further, the pair of stereo image sensors are configured to detect a subject placed over the object in the illuminated field of view. Further, the pair of stereo image sensors are configured to record a first stereo image of the subject from a first view point and a second stereo image of the subject from a second view point in the illuminated field of view. Further, the stereo-visual localization apparatus includes a stereo-visual localization controller configured to generate a stereo-visual user interface displaying the first stereo image of the subject and the second stereo image of the subject across the stereo image of the object. Further, the stereo-visual localization controller is configured to detect a movement of the subject in the field of view to align the subject with the object. Further, the stereo-visual localization controller is configured to visually align the subject with the object based on the movement by simultaneously changing apparent position of each of the first and the second stereo images of the subject in the stereo-visual interface.

Accordingly the embodiments herein provide a method for stereo-visual localization of an object by a portable apparatus. The method includes illuminating, by a pair of light source, a field of view in which the object is located, wherein the pair of light source is situated on a pair of support members which longitudinally sits in parallel on the field of view. Further, the method includes recording, by a pair of stereo image sensors, a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors, wherein the each of the stereo image sensors is situated on each of the support member. Further, the method includes detecting, by the pair of stereo image sensors, a subject placed over the object in the illuminated field of view. Furthermore, the method includes recording, by the pair of stereo image sensors, a first stereo image of the subject from the first view point by the first stereo image sensor and a second stereo image of the subject from the second view point by the second stereo image sensor. Further, the method includes generating, a stereo-visual user interface displaying the first stereo image of the object in a first portion and the second stereo image of the object in a second portion. Furthermore, the method includes analyzing the first stereo image of the object and the first stereo image of the object in the stereo-visual user interface.

In an embodiment, the method further includes a stereo-visual localization apparatus operably coupled with the portable apparatus. The stereo-visual localization apparatus is configured for generating, by a stereo-visual localization apparatus, a stereo-visual interface displaying the first stereo image of the object and the first stereo image of the subject in a first portion and the second stereo image of the object and the second stereo image of the subject in a second portion. Further, the stereo-visual localization apparatus is configured for detecting, by the stereo-visual localization apparatus, a movement of the subject to align the subject in the field of view with the object. Further, the stereo-visual localization apparatus is configured for visually aligning, by the stereo-visual localization apparatus, the subject with the object based on the movement by simultaneously changing apparent position of the first and the second stereo images of the subject in each of the first portion and the second portion in the stereo-visual interface.

In an embodiment, the method further includes a stereo-visual localization apparatus operably coupled with the portable apparatus. The stereo-visual localization apparatus is configured for generating a stereo-visual user interface displaying the first stereo image of the subject and the second stereo image of the subject across the stereo image of the object. Further, the stereo-visual localization apparatus is configured for detecting a movement of the subject in the field of view to align the subject with the object. Further, the stereo-visual localization apparatus is configured for visually aligning the subject with the object based on the movement by simultaneously changing apparent position of each of the first and the second stereo images of the subject in the stereo-visual interface.

Accordingly the embodiments herein provide a method for stereo-visual localization of an object by a stereo-visual localization apparatus. The method includes generating, by a stereo-visual localization apparatus, a stereo-visual interface displaying the first stereo image of the object and the first stereo image of the subject in a first portion and the second stereo image of the object and the second stereo image of the subject in a second portion. Further, the method includes detecting, by the stereo-visual localization apparatus, a movement of the subject to align the subject in the field of view with the object. Furthermore, the method includes visually aligning, by the stereo-visual localization apparatus, the subject with the object based on the movement by simultaneously changing apparent position of the first and the second stereo images of the subject in each of the first portion and the second portion in the stereo-visual interface.

In an embodiment, the method further includes a portable apparatus operably coupled with stereo-visual localization apparatus. The portable apparatus is configured for illuminating, by a pair of light source, a field of view in which the object is located, wherein the pair of light source is situated on a pair of support members which longitudinally sits in parallel on the field of view. Further, the portable apparatus is configured for recording, by a pair of stereo image sensors, a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors, wherein the each of the stereo image sensors is situated on each of the support member. Further, the portable apparatus is configured for detecting, by the pair of stereo image sensors, a subject placed over the object in the illuminated field of view. Further, the portable apparatus is configured for recording, by the pair of stereo image sensors, a first stereo image of the subject from the first view point by the first stereo image sensor and a second stereo image of the subject from the second view point by the second stereo image sensor.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF DRAWINGS

This method is illustrated in the accompanying drawings, throughout which like reference letters indicate corresponding parts in the various figures. The embodiments herein will be better understood from the following description with reference to the drawings, in which:

FIG. 1 is an example illustration of a vein detector, according to a prior art;

FIG. 2a-2c are example illustrations of a system in which a portable apparatus is connected to a stereo-visual localization apparatus for stereo-visual localization of an object, according to an embodiment as disclosed herein;

FIGS. 3a-3c are example illustrations of the portable apparatus, according to an embodiment as disclosed herein;

FIG. 4a is a block diagram illustrating various hardware components of the stereo-visual localization apparatus, according to an embodiment as disclosed herein;

FIG. 4b is a block diagram illustrating various hardware components of the stereo-visual localization apparatus, according to an embodiment as disclosed herein;

FIG. 5 is a block diagram illustrating various hardware components of a stereo-visual localization controller of the stereo-visual localization apparatus, according to an embodiment as disclosed herein;

FIG. 6 is a sequence diagram illustrating various signaling messages communicated between the portable apparatus and the stereo-visual localization apparatus for stereo-visual localization of the object, according to an embodiment as disclosed herein;

FIG. 7a is a flow diagram illustrating various operations for stereo-visual localization of an object, according to an embodiment as disclosed herein;

FIG. 7b is a flow diagram illustrating various operations for visually aligning a subject with the object in a single axis based on a parallax of the object and a parallax of the subject, according to an embodiment as disclosed herein;

FIGS. 8a-8c are example illustrations in which the stereo-visual localization apparatus aligns the subject with the object in the single axis, according to an embodiment as disclosed herein;

FIGS. 9a-9c are example illustrations in which the stereo-visual localization apparatus aligns the subject with the object in the single axis, according to an embodiment as disclosed herein;

FIG. 10a is a flow diagram illustrating various operations for stereo-visual localization of the object, according to an embodiment as disclosed herein;

FIG. 10b is a flow diagram illustrating various operations for visually aligning the subject with the object in the single axis based on the parallax of the object and the parallax of the subject, according to an embodiment as disclosed herein;

FIGS. 11a-11e are example illustrations in which the stereo-visual localization apparatus aligns the subject with the object in the single axis, according to an embodiment as disclosed herein;

FIGS. 12a-12e are example illustrations in which the stereo-visual localization apparatus aligns the subject with the object in the single axis, according to an embodiment as disclosed herein;

FIG. 13 is a flow diagram illustrating various operations for stereo-visual localization of the object, according to an embodiment as disclosed herein;

FIG. 14a is an example illustration of a microphotography device, according to a prior art;

FIG. 14b is an example illustration of the stereo-visual localization apparatus for obtaining a micro-photographic image (under illumination wavelength like NIR, FIR, Ultraviolet, etc.), according to an embodiment as disclosed herein;

FIG. 15a is an example illustration of an ultrasound imaging device, according to a prior art; and FIG. 15b is an example illustration of the stereo-visual localization apparatus for displaying the ultrasound images, according to an embodiment as disclosed herein.

MODE FOR THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

As is traditional in the field, embodiments may be described and illustrated in terms of blocks which carry out a described function or functions. These blocks, which may be referred to herein as managers, units, modules, hardware components or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

Accordingly the embodiments herein provide a system for stereo-visual localization of an object. The system includes a portable apparatus operably coupled with a stereo-visual localization apparatus. The portable apparatus includes a pair of support members which longitudinally sits in parallel on a field of view in which the object is located. Further, the portable apparatus includes pair of light source, each of which is situated on each of the support members, configured to illuminate the field of view in which the object is located. Further, the portable apparatus includes a pair of stereo image sensors placed over the object, each of the stereo image sensors is situated on each of the support members. The pair of stereo image sensors are configured to record a first stereo image of the object in the illuminated field of view from a first view point by a first stereo image sensor of the pair of stereo image sensors and a second stereo image of the object in the illuminated field of view from a second view point by a second stereo image sensor of the pair of stereo image sensors.

Unlike conventional systems and methods, the proposed system can be used to visualize a vein of the patient in real time. The proposed system includes a portable apparatus which includes the pair of light source for illuminating the vein and further, the pair of stereo image sensors which are placed in proximity with the vein can be used for capturing the stereo images of the vein. Further, the proposed system can be used to visualize the captured stereo images of the vein in a three dimensional (3D) view. Further, the proposed system can be used to detect a needle placed over the vein and can align the needle with the vein in a single axis. This alignment can result in determining the location of the vein accurately.

Unlike conventional systems and methods, the proposed system allows a medical practitioner/clinician to view an exact location of the object in real time using the stereo-visual localization apparatus (e.g., head mounted display). Further, the medical practitioner can precisely align the subject into the axis of the object with ease.

The proposed system can be used to illuminate the vein using the pair of light sources. Thus, the proposed system can be used to view the vein, which are normally invisible to the naked eye. The medical practitioner can view the vein in a stereo interface and perform a needle insertion for any intravenous procedures. This can result in reducing needle insertion attempts, as the medical practitioner locates the vein with ease. This results in achieving a single needle insertion for vein puncturing. Hence, the proposed system can be used to increase a patient safety and provides a comfort for the patient.

Unlike conventional systems and methods, the proposed system ensures that the pair of stereo image sensors are placed in proximity of the field of view of a user skin. The arrangement of pair of stereo image sensors can reduce the difference between a parallax of the needle and the vein to zero, which results in high accuracy of locating the vein.

The proposed system can be used to localize the vein based on a relative geometry change of parallax images of the needle and vein using the pair of stereo image sensor. This allows the medical practitioner to safely, precisely maneuver and align the needle exactly into the axis of a vein. Further, the stereo image sensor based alignment of the vein and needle image is more accurate, since the 0.1 mm gap between needle and vein is highly visually magnified by closeness of the pair of two cameras to the gap. A magnified view of the needle and the vein can be visualized by the medical practitioner using the head mounted display in real time. The magnified view can be in the Near Infrared (NIR) to Far Infrared (FIR) range, ultraviolet, which depends on the pair of stereo image sensor and the light source used. This enhances the accuracy in determining the exact location of the vein.

The proposed system can be used to visualize a deeper view of any buried structure (e.g., vein, femoral artery, bone, or the like). For example, the system of wearable apparatus and the stereo-visual localization apparatus can be used for ultrasound imaging of blood vessels, and further for precise, magnified, stereo-3D based cannulation of a deeply placed large vein as is needed in a critical surgery.

Referring now to the drawings, and more particularly to FIGS. 2a through 13, FIG. 14b and FIG. 15b, there are shown preferred embodiments.

FIG. 2a-2c are example illustrations of a system 1000 in which a portable apparatus 100 is connected to a stereo-visual localization apparatus 200 for stereo-visual localization of an object, according to an embodiment as disclosed herein.

As shown in the FIG. 2a, the system 1000 includes the portable apparatus 100 in communication with the stereo-visual localization apparatus 200. In an example, the stereo-visual localization apparatus 200 can be a head mounted display (HMD) device, Gear-Virtual Reality (VR) HMD, or the like.

In an embodiment, the portable apparatus 100 is configured to be worn by a medical practitioner (e.g., clinician). The portable apparatus 100 includes a pair of support members (100a-100b) which longitudinally sits in parallel on a field of view in which the object is located. In an embodiment, the object is a buried structure beneath a user skin. For example, the object can be a vein, an artery, a capillary or the like. In another embodiment, the object can be a micro-organism inside a sample/specimen, a flower, an insect, or the like.

In an embodiment, the portable apparatus 100 includes a pair of light source (102a-102b), each of which is situated on each of the support members. The pair of light source (102a-102b) are configured to illuminate the field of view in which the vein is located. In an embodiment, the pair of light source (102a-102b) can be Light Emitting Diode (LED), infrared LED, or the like.

In an embodiment, the portable apparatus 100 further includes a fastening band 112 (as shown in FIG. 2c) to fasten the portable apparatus to the user skin. In an example, the fastening band is a Velcro-based fastening band. Further, the portable apparatus 100 includes a supporting member to provide a support to a subject, in which the supporting member includes a notch-depression for resting the subject to align with the vein. In an example, the subject is a needle, syringe, cannula or the like.

In an embodiment, the portable apparatus 100 includes a pair of stereo image sensors (104a-104b) placed over the vein, each of the stereo image sensors is situated on each of the support members. In an example, the stereo image sensor can be a camera, Charge Coupled Device (CCD) sensor, or the like. The pair of stereo image sensors (104a-104b) are configured to record a first stereo image of the vein in the illuminated field of view from a first view point by a first stereo image sensor of the pair of stereo image sensors and a second stereo image of the vein in the illuminated field of view from a second view point by a second stereo image sensor of the pair of stereo image sensors.

In an embodiment, the first view point and the second view point can be at least one of a left side view and a right side view.

In an embodiment, the pair of stereo image sensors (104a-104b) are configured to detect the subject (i.e., needle) placed over the vein in the illuminated field of view. Further, the pair of stereo image sensors (104a-104b) are configured to record a first stereo image of the needle from the first view point by the first stereo image sensor and a second stereo image of the needle from the second view point by the second stereo image sensor.

In an embodiment, the stereo-visual localization apparatus 200 is operably coupled to the portable apparatus 100. The stereo-visual localization apparatus 200 is configured to generate a stereo-visual interface displaying the first stereo image of the vein and the first stereo image of the needle in a first portion and the second stereo image of the vein and the second stereo image of the needle in a second portion (as shown in the FIG. 8a-8b).

In an embodiment, the stereo-visual localization apparatus 200 detects a movement of the needle to align the needle in the field of view with the vein. Further, the stereo-visual localization apparatus 200 visually aligns the needle with the vein based on the movement by simultaneously changing apparent position of the first and the second stereo images of the needle in each of the first portion and the second portion in the stereo-visual interface.

In an embodiment, the stereo-visual localization apparatus 200 aligns the needle in the field of view with the vein based on an equal-parallax-principle, thus without using any 3D scene reconstruction. The equal-parallax principle indicates that objects (e.g., needle/vein) at same depth will have the same disparity under the pair of stereo image sensor. The parallax of two linear objects will be same if and only if they are at the same depth under the pair of stereo image sensor. The parallax of the vein and the parallax of the needle will both be zero only if they are in a single axis (i.e. aligned for insertion)

In an embodiment, the stereo-visual localization apparatus 200 determines a difference in the apparent position of the vein viewed along the first view point and the second view point based on the movement of the vein. Further, the stereo-visual localization apparatus 200 determines a parallax of the vein based on the difference in the apparent position of the vein viewed along the first view point and the second view point. Further, the stereo-visual localization apparatus 200 determines a difference in an apparent position of the needle viewed along the first view point and the second view point based on the movement of the needle. Further, the stereo-visual localization apparatus 200 determines a parallax of the needle based on the difference in the apparent position of the needle viewed along the first view point and the second view point. In an embodiment, the parallax of the vein and the parallax of the needle is zero when the vein and the needle are in the single axis.

In an embodiment, the vein has an unknown tilt/angle inside the user skin, making it very difficult to estimate (e.g. stroke risk from carotid artery) blood flow velocity with a Doppler (even with non-90 degree probe tilt). This life-critical blood velocity estimation becomes almost trivial with the stereo image sensor. The two Doppler probes can be used to record the image at a different tilt or angle of the artery or vein from a different position in space (e.g., first point of view/second point of view). Hence, a true tilt/angle with respect to the user skin can be inferred from a 2-probe Doppler geometry. The stereo image relative tilt will give the artery/vein angle.

Furthermore, the stereo-visual localization apparatus 200 visually aligns the needle with the vein in a single axis based on the parallax of the vein and the parallax of the needle in both the first portion and the second portion of the stereo-visual interface. In an embodiment, the first stereo image of the needle appears on a left side of the first stereo image of the vein in the first portion of the stereo-visual user interface, and the second stereo image of the needle appears on a right side of the second stereo image of the vein in the second portion of the stereo-visual user interface (as shown in the FIG. 8c).

As shown in the FIG. 2b, the system 1000 includes the portable apparatus 100 in communication with the stereo-visual localization apparatus 200. In an example, the stereo-visual localization apparatus 200 can be a smartphone. The portable apparatus 100 includes the pair of support members (100a-100b) which longitudinally sits in parallel on the field of view in which the vein is located. In an embodiment, the portable apparatus 100 further includes the fastening band to fasten the portable apparatus to the user skin. Further, the portable apparatus 100 includes a supporting member to provide a support to the needle, in which the supporting member includes a notch-depression for resting the needle to align with the vein.

In an embodiment, the stereo-visual localization apparatus 200 (e.g., smartphone) includes a pair of stereo image sensors (104a-104b) which are in proximity with the portable device 100 and the vein. In an embodiment, the stereo-visual localization apparatus 200 captures a first image of the vein from a first view point and a second image of the vein from a second view point in the illuminated field of view. Further, the stereo-visual localization apparatus 200 determines pixels corresponding to the vein in the first image and pixels corresponding to the vein in the second image. Furthermore, the stereo-visual localization apparatus 200 records the stereo image of the vein by combining the pixels corresponding to the vein in the first image with the pixels corresponding to the vein in the second image (as shown in the FIG. 11b).

Further, the pair of stereo image sensors are configured to detect the needle placed over the vein in the illuminated field of view. Further, the pair of stereo image sensors are configured to record a first stereo image of the needle from a first view point and a second stereo image of the needle from a second view point in the illuminated field of view. Further, the stereo-visual localization apparatus 200 configured to generate the stereo-visual user interface (as shown in the FIG. 11a-11e) displaying the first stereo image of the needle and the second stereo image of the needle across the stereo image of the vein. Further, the stereo-visual localization apparatus 200 configured to detect a movement of the needle in the field of view to align the needle with the vein. Further, the stereo-visual localization apparatus 200 visually aligns the needle with the vein based on the movement by simultaneously changing apparent position of each of the first and the second stereo images of the needle in the stereo-visual interface.

In an embodiment, the stereo-visual localization apparatus 200 determines the difference in the apparent position of the needle viewed along the first view point and the second view point based on the movement of the needle in the field of view. Further, the stereo-visual localization apparatus 200 determines the parallax of the first stereo image and the second stereo image of the needle based on the difference in the apparent position of the needle. Further, the stereo-visual localization apparatus 200 visually aligns the needle with the vein in a single axis based on the parallax of first and second stereo images of the needle. In an embodiment, the parallax of the first and second stereo images of the needle is zero when the vein and the needle are in the single axis (as shown in the FIG. 11e).

As shown in the FIG. 2c, the system 1000 includes the portable apparatus 100 in communication with the stereo-visual localization apparatus 200. In an example, the stereo-visual localization apparatus 200 can be the HMD device. In an embodiment, the portable apparatus 100 includes the pair of support members (100a-100b) which longitudinally sits in parallel on a field of view in which the vein is located. Further, the portable apparatus 100 includes the pair of light source (102a-102b), each of which is situated on each of the support members. The pair of light source (102a-102b) are configured to illuminate the field of view in which the vein is located. Further, the portable apparatus 100 includes the pair of stereo image sensors (104a-104b) placed over the vein, wherein each of the stereo image sensors is situated on each of the support members, configured to record the first stereo image of the vein from a first view point and the second stereo image of the vein from the second view point in the illuminated field of view.

In an embodiment, the stereo-visual localization apparatus 200 configured to generate the stereo-visual user interface displaying the first stereo image of the vein in the first portion and the second stereo image of the vein in the second portion. In an example, the image sensors is one of a stereo-camera device and an ultrasound device.

Consider an example scenario in which the patient is an obese person and it is very difficult for the clinician to locate the vein in his/her hand. The clinician can use the pair thimbles on one hand to illuminate the field of the view of the patient hand. Further, the pair of thimbles includes the pair of stereo image sensors for recording the first and second stereo image of the vein. The head mounted display 200 worn on a clinician head can display the first and second stereo image of the vein. Further, the clinician can bring the needle inside the field of view. The pair of stereo image sensors records the first and second stereo image of the needle. Further, the clinician can gently align the needle towards the vein of the patient, which results in aligning the first and second stereo image of the needle with the first and second stereo image of the vein. The clinician can perform the alignment until the first and second stereo image of the needle are in single axis with the first and second stereo image of the vein.

FIGS. 3a-3c are example illustrations of the portable apparatus, according to an embodiment as disclosed herein. In an embodiment, as shown in the FIG. 3a, the portable apparatus 100 is a pair of thimbles for performing the localization of the vein. The pair of thimbles has the pair of support members (100a-100b) which can be worn by the medical practitioner on his/her hand. The pair of support members (100a-100b) includes an array of light source (102*a*-102*b*). In an embodiment, the array of light source (102*a*-102*b*) are placed on a down portion of the pair of support members (100*a*-100*b*). Further, each of the support members (100*a*-100*b*) includes each of stereo image sensors for capturing the first stereo image and the second stereo image of the vein.

In an embodiment, as shown in the FIG. 3*b*, the portable apparatus 100 is a clip structure, where the clip structure includes the pair of support members (100*a*-100*b*). The clip structure can be affixed to the user skin (e.g., patient) using the fastening band 112. In an example, the fastening band 112 can be a Velcro band, an elastomeric strap, or the like. The fastening band 112 can be coupled to the user skin on a desired spot (for e.g., thighs, stomach, etc.). Further, in order to align a longitudinal gap between the clip arms to the vein that may run at different angle, the clip structure can be made rotatable to any arbitrary angle to the arm. The clip structure includes the pair of light source (not shown) for illuminating the vein in the field of view. Further, clip structure includes the pair of stereo image sensors (104*a*-104*b*) for capturing the first stereo image and the second stereo image of the vein. Further, the clip structure includes a supporting member 106 for providing a support to the needle. The supporting member 106 includes a notch-depression for resting the subject to align with the object.

In an embodiment, as shown in the FIG. 3*c*, the portable apparatus 100 is the clip structure, where the clip structure includes the pair of support members (100*a*-100*b*). In an example, the pair of support members (100*a*-100*b*) can be a probe structure. The clip structure can be affixed on a portable stand for taking a microphotography of the object (e.g., micro-organism). The clip structure includes the pair of light source (not shown) for illuminating the vein in the field of view (in any desired wavelength). Further, clip structure includes the pair of stereo image sensors (104*a*-104*b*) for capturing the first stereo image and the second stereo image of the vein. The system can also be used inexpensively through a smartphone to record a time-lapse or a slow-motion stereo micro photography of the said organism as it grows and multiplies.

FIG. 4*a* is a block diagram illustrating various hardware components of the stereo-visual localization apparatus 200, according to an embodiment as disclosed herein. In an embodiment, the stereo-visual localization apparatus 200 includes a transceiver 210, a stereo-visual localization controller 220, a communication interface 230, a memory 240, a processor 250, and a display 260. In an embodiment, the stereo-visual localization apparatus 200 can be the head mounted display device.

In an embodiment, the transceiver 210 is configured to receive the first stereo image of the vein in the illuminated field of view from the first view point by the first stereo image sensor 104*a* of the pair of stereo image sensors (104*a*-104*b*) and the second stereo image of the vein in the illuminated field of view from the second view point by the second stereo image sensor 104*b* of the pair of stereo image sensors (104*a*-104*b*). Further, the transceiver 210 is configured to receive first stereo image of the needle from the first view point by the first stereo image sensor 104*a* and the second stereo image of the needle from the second view point by the second stereo image sensor 104*b*.

In an embodiment, the stereo-visual localization controller 220 generates the stereo-visual interface on the display 260, the stereo-visual interface displays the first stereo image of the vein and the first stereo image of the needle in a first portion and the second stereo image of the vein and the second stereo image of the needle in a second portion.

In an embodiment, the stereo-visual localization controller 220 detects the movement of the needle to align the needle in the field of view with the vein. In an embodiment, the stereo-visual localization controller 220 determines the difference in the apparent position of the vein viewed along the first view point and the second view point based on the movement of the vein. Further, the stereo-visual localization controller 220 determines the parallax of the vein based on the difference in the apparent position of the vein viewed along the first view point and the second view point. Further, the stereo-visual localization controller 220 determines the difference in the apparent position of the needle viewed along the first view point and the second view point based on the movement of the needle.

Further, the stereo-visual localization controller 220 determines the parallax of the needle based on the difference in the apparent position of the needle viewed along the first view point and the second view point. In an embodiment, the parallax of the vein and the parallax of the needle is zero when the vein and the needle are in the single axis. Further, the stereo-visual localization controller 220 visually aligns the needle with the vein based on the movement by simultaneously changing apparent position of the first and the second stereo images of the needle in each of the first portion and the second portion in the stereo-visual interface.

Furthermore, the stereo-visual localization controller 220 visually aligns the needle with the vein in the single axis based on the parallax of the vein and the parallax of the needle in both the first portion and the second portion of the stereo-visual interface. In an embodiment, the first stereo image of the needle appears on the left side of the first stereo image of the vein in the first portion of the stereo-visual user interface, and the second stereo image of the needle appears on the right side of the second stereo image of the vein in the second portion of the stereo-visual user interface.

In an embodiment, the communication interface 230 is configured to communicate with the portable apparatus 100 for receiving the first and second stereo image of the vein, and the first and second stereo image of the needle.

In an embodiment, the processor 250 is coupled with the memory 240 for processing various instructions stored in the memory 240 to perform the stereo-visual localization of the vein.

The memory 240 can be configured to store the user profile and usage history of the user. The memory 240 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 240 may, in some examples, be considered a non-transitory storage medium. The term "non-transitory" may indicate that the storage medium is not embodied in a carrier wave or a propagated signal. However, the term "non-transitory" should not be interpreted that the memory 240 is non-movable. In some examples, the memory 240 can be configured to store larger amounts of information than the memory. In certain examples, a non-transitory storage medium may store data that can, over time, change (e.g., in Random Access Memory (RAM) or cache).

The display 260 can be configured to generate the stereo-visual interface displaying the first stereo image of the vein and the first stereo image of the needle in the first portion, and the second stereo image of the vein and the second stereo image of the needle in the first portion. Further, the display 260 can be configured to display the visually aligned stereo image of the vein and the needle. The display 260 can be, for example, but not limited to a Liquid Crystal Display (LCD), an Active Matrix Organic Light Emitting Diode (AM-OLED) display, a Light Emitting Diode (LED) display, or the like.

Although the FIG. 4a shows various hardware components of the stereo-visual localization apparatus 200 but it is to be understood that other embodiments are not limited thereon. In other embodiments, the stereo-visual localization apparatus 200 may include less or more number of components. Further, the labels or names of the components are used only for illustrative purpose and does not limit the scope of the invention. One or more components can be combined together to perform same or substantially similar function of stereo-visual localization of the vein on the stereo-visual localization apparatus 200.

FIG. 4b is a block diagram illustrating various hardware components of the stereo-visual localization apparatus 200, according to an embodiment as disclosed herein. In an embodiment, the stereo-visual localization apparatus 200 is the smartphone. In an embodiment, the stereo-visual localization apparatus 200 includes the transceiver 210, the stereo-visual localization controller 220, the communication interface 230, the memory 240, the processor 250, and the display 260 and the pair of image sensor 104. The smartphone 200 uses an in-build dual cameras to visualize the vein and the needle.

In an embodiment, the transceiver 210 is configured to communicate with the internal hardware components of the stereo-visual localization apparatus 200. For example, the image sensor 104 communicates with the stereo-visual localization controller 220 via the transceiver 210.

In an embodiment, the stereo-visual localization controller 220 generates the stereo-visual interface on the display 260, the stereo-visual interface displays the first stereo image of the vein and the first stereo image of the needle in the first portion and the second stereo image of the vein and the second stereo image of the needle in the second portion.

In an embodiment, the stereo-visual localization apparatus 200 (e.g., smartphone) includes the pair of stereo image sensors (104a-104b) which are in proximity with the portable device 100 and the vein. In an embodiment, the pair of stereo image sensors (104a-104b) captures the first image of the vein from the first view point and the second image of the vein from the second view point in the illuminated field of view. Further, the stereo-visual localization controller 220 determines pixels corresponding to the vein in the first image and pixels corresponding to the vein in the second image. Furthermore, the stereo-visual localization controller 220 records the stereo image of the vein by combining the pixels corresponding to the vein in the first image with the pixels corresponding to the vein in the second image.

Further, the pair of stereo image sensors (104a-104b) are configured to detect the needle placed over the vein in the illuminated field of view. Further, the pair of stereo image sensors (104a-104b) are configured to record the first stereo image of the needle from the first view point and the second stereo image of the needle from the second view point in the illuminated field of view. Further, the stereo-visual localization controller 220 is configured to generate the stereo-visual user interface (as shown in the FIG. 11a-11e) displaying the first stereo image of the needle and the second stereo image of the needle across the stereo image of the vein. Further, the stereo-visual localization controller 220 is configured to detect a movement of the needle in the field of view to align the needle with the vein. Further, the stereo-visual localization controller 220 visually aligns the needle with the vein based on the movement by simultaneously changing apparent position of each of the first and the second stereo images of the needle in the stereo-visual interface.

In an embodiment, the stereo-visual localization controller 220 determines the difference in the apparent position of the needle viewed along the first view point and the second view point based on the movement of the needle in the field of view. Further, the stereo-visual localization controller 220 determines the parallax of the first stereo image and the second stereo image of the needle based on the difference in the apparent position of the needle. Further, the stereo-visual localization controller 220 visually aligns the needle with the vein in a single axis based on the parallax of first and second stereo images of the needle. In an embodiment, the parallax of the first and second stereo images of the needle is zero when the vein and the needle are in the single axis.

In an embodiment, the communication interface 230 is configured to communicate with the portable apparatus 100. For example, the stereo-localization apparatus can communicate the amount of light required for illuminating the vein with the portable apparatus.

In an embodiment, the processor 250 is coupled with the memory 240 for processing various instructions stored in the memory 240 to perform the stereo-visual localization of the vein.

The memory 240 can be configured to store the user profile and usage history of the user. The memory 240 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 240 may, in some examples, be considered a non-transitory storage medium. The term "non-transitory" may indicate that the storage medium is not embodied in a carrier wave or a propagated signal. However, the term "non-transitory" should not be interpreted that the memory 240 is non-movable. In some examples, the memory 240 can be configured to store larger amounts of information than the memory. In certain examples, a non-transitory storage medium may store data that can, over time, change (e.g., in Random Access Memory (RAM) or cache).

The display 260 can be configured to generate the stereo-visual interface displaying the first stereo image of the vein and the first stereo image of the needle in the first portion, and the second stereo image of the vein and the second stereo image of the needle in the first portion. Further, the display 260 can be configured to display the visually aligned stereo image of the vein and the needle. The display 260 can be, for example, but not limited to a Liquid Crystal Display (LCD), an Active Matrix Organic Light Emitting Diode (AM-OLED) display, a Light Emitting Diode (LED) display, or the like.

Although the FIG. 4b shows various hardware components of the stereo-visual localization apparatus 200 but it is to be understood that other embodiments are not limited thereon. In other embodiments, the stereo-visual localization apparatus 200 may include less or more number of components. Further, the labels or names of the components are used only for illustrative purpose and does not limit the scope of the invention. One or more components can be combined together to perform same or substantially similar function of stereo-visual localization of the vein on the stereo-visual localization apparatus 200.

FIG. 5 is a block diagram illustrating various hardware components of the stereo-visual localization controller 220 of the stereo-visual localization apparatus 200, according to an embodiment as disclosed herein. In an embodiment, the stereo-visual localization controller 220 includes a stereo visual representation generator 221, an object recognizer 222, an event detector 223, a subject recognizer 224, a parallax controller 225 and an alignment controller 226.

In an embodiment, the stereo visual representation generator 221 is configured to generate the stereo-visual interface displaying the first stereo image of the vein and the first stereo image of the needle in the first portion and the second stereo image of the vein and the second stereo image of the needle in a second portion.

Further, the object recognizer 222 can recognize the object in the stereo-visual interface. In an embodiment, the event detector 223 is configured to detect the event of the vein and the needle. In an example, the event can be a vein-alignment event in the stereo-visual interface. In another example, the event can be a needle-alignment with respect to the vein in the stereo-visual interface.

In an embodiment, the subject recognizer 224 detects the movement of the needle to align the needle in the field of view with the vein. Further, the alignment controller 226 visually aligns the needle with the vein based on the movement by simultaneously changing apparent position of the first and the second stereo images of the needle in each of the first portion and the second portion in the stereo-visual interface.

In an embodiment, the parallax controller 225 determines the difference in the apparent position of the vein viewed along the first view point and the second view point based on the movement of the vein. Further, the parallax controller 225 determines the parallax of the vein based on the difference in the apparent position of the vein viewed along the first view point and the second view point. Further, the parallax controller 225 determines the difference in the apparent position of the needle viewed along the first view point and the second view point based on the movement of the needle. Further, the parallax controller 225 determines the parallax of the needle based on the difference in the apparent position of the needle viewed along the first view point and the second view point. In an embodiment, the parallax of the vein and the parallax of the needle is zero when the vein and the needle are in the single axis.

Furthermore, the alignment controller 226 visually aligns the needle with the vein in the single axis based on the parallax of the vein and the parallax of the needle in both the first portion and the second portion of the stereo-visual interface. In an embodiment, the first stereo image of the needle appears on the left side of the first stereo image of the vein in the first portion of the stereo-visual user interface, and the second stereo image of the needle appears on the right side of the second stereo image of the vein in the second portion of the stereo-visual user interface.

In another embodiment, the stereo visual representation generator 221 generates the stereo-visual user interface displaying the first stereo image of the needle and the second stereo image of the needle across the stereo image of the vein. Further, the event detector 223 configured to detect a movement of the needle in the field of view to align the needle with the vein.

In an embodiment, the parallax controller 225 determines the difference in the apparent position of the needle viewed along the first view point and the second view point based on the movement of the needle in the field of view. Further, the parallax controller 225 determines the parallax of the first stereo image and the second stereo image of the needle based on the difference in the apparent position of the needle. Further, the alignment controller 226 visually aligns the needle with the vein in a single axis based on the parallax of first and second stereo images of the needle. In an embodiment, parallax of the first and second stereo images of the needle is zero when the vein and the needle are in the single axis. The alignment controller 226 visually aligns the needle with the vein based on the movement by simultaneously changing apparent position of each of the first and the second stereo images of the needle in the stereo-visual interface 202.

FIG. 6 is a sequence diagram illustrating various signaling messages communicated between the portable apparatus 100 and the stereo-visual localization apparatus 200 for stereo-visual localization of the vein, according to an embodiment as disclosed herein.

The portable apparatus includes the pair of support members (100a-100b). The pair of support members (100a-100b) includes an array of light source (102a-102b) to illuminate the vein in the field of view at step 602. Further, in response to the illumination, the first stereo image sensor 104a from the pair of stereo image sensors (104a-104b) records the first stereo image of the vein from the first view point. Further, the second stereo image sensor 104b from the pair of stereo image sensors (104a-104b) records the second stereo image of the vein from the second view point.

After recording, the first stereo image sensor 104a transmits the first stereo image of the vein from the first view point to the stereo-visual localization apparatus at step 604. The second stereo image sensor 104b transmits the second stereo image of the vein from the second view point to the stereo-visual localization apparatus at step 606.

The pair of stereo image sensors (104a-104b) detect the needle placed above the vein at step 608. Further, the first stereo image sensor 104a transmits the first stereo image of the needle from the first view point to the stereo-visual localization apparatus at step 610. The second stereo image sensor 104b transmits the second stereo image of the needle from the second view point to the stereo-visual localization apparatus at step 612.

The stereo-visual localization apparatus 200 generates the stereo-visual interface displaying the first stereo image of the vein and the first stereo image of the needle in the first portion and the second stereo image of the vein and the second stereo image of the needle in the second portion at step 614.

Further, the pair of stereo image sensors (104a-104b) detect the movement of the needle to align the needle with the vein at step 616. Based on the detection of the movement of the needle, the stereo-visual localization apparatus 200 visually aligns the needle with the vein at step 618.

Furthermore, the stereo-visual localization apparatus 200 displays the aligned stereo image of the needle and the vein on the display 260.

FIG. 7a is a flow diagram 700 illustrating various operations for stereo-visual localization of the object, according to an embodiment as disclosed herein. In an embodiment, the object is the needle, and the stereo visual localization apparatus 200 is the head mounted display.

At 710, the method includes illuminating, by the pair of light source (102a-102b), the field of view in which the object is located, wherein the pair of light source (102a-102b) is situated on the pair of support members which longitudinally sits in parallel on the field of view.

At 720, the method includes recording, by the pair of stereo image sensors, the first stereo image of the object in the illuminated field of view from the first view point by the first stereo image sensor of the pair of stereo image sensors and the second stereo image of the object in the illuminated field of view from the second view point by the second stereo image sensor of the pair of stereo image sensors.

At 730, the method includes detecting, by the pair of stereo image sensors, the subject placed over the object in the illuminated field of view. At 740, the method includes recording, by the pair of stereo image sensors, a first stereo image of the subject from the first view point by the first stereo image sensor and a second stereo image of the subject from the second view point by the second stereo image sensor. At 750, the method includes generating, by the stereo-visual localization apparatus 200, a stereo-visual interface displaying the first stereo image of the object and the first stereo image of the subject in a first portion and the second stereo image of the object and the second stereo image of the subject in a second portion.

At 760, the method includes detecting, by the stereo-visual localization apparatus, a movement of the subject to align the subject in the field of view with the object. At 770, the method includes visually align, by the stereo-visual localization apparatus, the subject with the object based on the movement by simultaneously changing apparent position of the first and the second stereo images of the subject in each of the first portion and the second portion in the stereo-visual interface.

The various actions, acts, blocks, steps, or the like in the flow diagram 700 may be performed in the order presented, in a different order or simultaneously. Further, in some embodiments, some of the actions, acts, blocks, steps, or the like may be omitted, added, modified, skipped, or the like without departing from the scope of the invention.

FIG. 7b is a flow diagram 770 illustrating various operations for visually aligning the subject with the object in the single axis based on the parallax of the object and the parallax of the subject, according to an embodiment as disclosed herein.

At 771, the method includes determining the difference in the apparent position of the object viewed along the first view point and the second view point based on the movement of the object. In an embodiment, the method allows the parallax controller 225 to determine the difference in the apparent position of the object viewed along the first view point and the second view point based on the movement of the object.

At 772, the method includes determining the parallax of the object based on the difference in the apparent position of the object viewed along the first view point and the second view point. In an embodiment, the method allows the parallax controller 225 to determine the parallax of the object based on the difference in the apparent position of the object viewed along the first view point and the second view point.

At 773, the method includes determining a difference in the apparent position of the subject viewed along the first view point and the second view point based on the movement of the subject. In an embodiment, the method allows the parallax controller 225 to determining the difference in the apparent position of the subject viewed along the first view point and the second view point based on the movement of the subject.

At 774, the method includes visually aligning the subject with the object in the single axis based on the parallax of the object and the parallax of the subject in both the first portion and the second portion of the stereo-visual interface. In an embodiment, the method allows the alignment controller 226 to visually aligning the subject with the object in the single axis based on the parallax of the object and the parallax of the subject in both the first portion and the second portion of the stereo-visual interface.

The various actions, acts, blocks, steps, or the like in the flow diagram 770 may be performed in the order presented, in a different order or simultaneously. Further, in some embodiments, some of the actions, acts, blocks, steps, or the like may be omitted, added, modified, skipped, or the like without departing from the scope of the invention.

FIGS. 8a-8c are example illustrations in which the head mounted display 200 aligns the subject with the object in the single axis, according to an embodiment as disclosed herein.

Consider an example scenario in which the head mounted display 200 can be used to visualize the aligned image of the needle and the vein in the display 260 and the portable apparatus 100 is the clip structure. The clip structure 100 is coupled to the user skin using the fastening band. Further, the clip structure 100 having the pair of light source (102a-102b) for illuminating the vein 110 in the field of view. The clip structure 100 includes pair of stereo image sensors (104a-104b) which are placed in proximity to the user skin, can record the first stereo image of the vein 110 from the first point of view using the first stereo image sensor 104a and the second stereo image of the vein 110 from the second point of view using the second stereo image sensor 104a. The recorded image can be transmitted to the head mounted display 200 via the communication interface 230. As shown in the FIG. 8a, the first stereo image of the vein 110 and the second stereo image of the vein 110 are displayed on a first portion and the second portion of the display 260.

Let the medical practitioner carries the needle 120 in the field of view of the vein 110. The pair of stereo image sensors (104a-104b) detects the needle 120 in the field of view. Further the pair of stereo image sensors (104a-104b) record the first stereo image of the needle 120 from the first point of view using the first stereo image sensor 104a and the second stereo image of the needle 120 from the second point of view using the second stereo image sensor 104a. The needle 120 appears double in the stereo image due to the parallax. The recorded stereo image can be transmitted to the head mounted display 200 via the communication interface 230. As shown in the FIG. 8b, the first stereo image of the vein 110 and the first stereo image of the needle 120 are displayed on the first portion of the display 260, and the second stereo image of the vein 110 and the second stereo image of the needle 120 are displayed on the second portion of the display 260. Further, the pair of stereo image sensors (104a-104b) detect the movement of the needle 120 towards the vein 110 for reducing the parallax of the needle 120 as illustrated by arrow marks.

The medical practitioner can gently lower/adjust needle 120, until the first stereo image of needle 120 and the second stereo image of needle 120 aligns with the second stereo image of vein 110 and the second stereo image of vein 110. This alignment can be used to reduce the parallax of the needle and the parallax of the vein, as the stereo images are taken at the different view point. Further, as shown in the FIG. 8c, the first stereo image of the needle 120 is aligned with the first stereo image of the vein 110 and second stereo image of the needle 120 is aligned with the second stereo image of the vein 110. This allows the medical practitioner to clearly view the location of the vein and can perform the needle insertion accurately.

In another example, consider a scenario in which surgeon/medical practitioner can view an implanted bone plates based on the stereo-visual localization apparatus 200. The stereo-visual localization apparatus 200 can be used for viewing/aligning/localizing the objects in real time.

FIGS. 9a-9c are example illustrations in which the stereo-visual localization apparatus aligns the subject with the object in the single axis, according to an embodiment as disclosed herein.

Consider an example scenario in which the head mounted display 200 can be used to visualize the aligned image of the needle 120 and the vein 110 in the display 260 and the portable apparatus 100 is the pair of thimbles. The pair of thimbles 100 is placed in proximity with the field of view of the user skin. Further, the pair of thimbles 100 having the pair of light source (102a-102b) for illuminating the vein 110 in the field of view. The pair of thimbles 100 includes pair of stereo image sensors (104a-104b) which are placed in proximity to the user skin, can record the first stereo image of the vein 110 from the first point of view using the first stereo image sensor 104a and the second stereo image of the vein 110 from the second point of view using the second stereo image sensor 104a. The recorded image can be transmitted to the head mounted display 200 via the communication interface 230. As shown in the FIG. 9a, the first stereo image of the vein 110 and the second stereo image of the vein 110 are displayed on a first portion and the second portion of the display 260.

In conjunction with the FIG. 8b, let the medical practitioner carries the needle 120 in the field of view of the vein 110. As shown in the FIG. 9b, the first stereo image of the vein 110 and the first stereo image of the needle 120 are displayed on the first portion of the display 260, and the second stereo image of the vein 110 and the second stereo image of the needle 120 are displayed on the second portion of the display 260. Further, the pair of stereo image sensors (104a-104b) detect the movement of the needle 120 towards the vein 110 for reducing the parallax of the needle 120 as illustrated by arrow marks.

In conjunction with the FIG. 8c, the medical practitioner can gently lower/adjust needle 120, until the first stereo image of needle 120 and the second stereo image of needle 120 aligns with the second stereo image of vein 110 and the second stereo image of vein 110. Further, as shown in the FIG. 9c, the first stereo image of the needle 120 is aligned with the first stereo image of the vein 110 and second stereo image of the needle 120 is aligned with the second stereo image of the vein 110. This allows the medical practitioner to clearly view the location of the vein 110 and can perform the needle insertion accurately.

FIG. 10a is a flow diagram 800 illustrating various operations for stereo-visual localization of the object, according to an embodiment as disclosed herein. In an embodiment, the object is the needle, and the stereo visual localization apparatus 200 is the smartphone.

At 810, the method illuminating, by the pair of light source (102a-102b) of the wearable apparatus 100, a field of view in which the object is located. At 820, the method includes recording, by the pair of stereo image sensors (104a-104b) of the stereo-visual localization apparatus 200, a stereo image of the object in the illuminated field of view.

At 830, the method includes detecting, by the pair of stereo image sensors (104a-104b) of the stereo-visual localization apparatus, the subject placed over the object in the illuminated field of view. At 840, the method includes recording, by the pair of stereo image sensors (104a-104b) of the stereo-visual localization apparatus 200, a first stereo image of the subject from a first view point and a second stereo image of the subject from a second view point in the illuminated field of view.

At 850, the method includes generating, by the stereo-visual localization apparatus, a stereo-visual user interface displaying the first stereo image of the subject and the second stereo image of the subject across the stereo image of the object. At 860, the method includes detecting, by the stereo-visual localization apparatus, a movement of the subject in the field of view to align the subject with the object.

At 870, the method includes visually aligning, by the stereo-visual localization apparatus, the subject with the object based on the movement by simultaneously changing apparent position of each of the first and the second stereo images of the subject in the stereo-visual interface.

The various actions, acts, blocks, steps, or the like in the flow diagram 800 may be performed in the order presented, in a different order or simultaneously. Further, in some embodiments, some of the actions, acts, blocks, steps, or the like may be omitted, added, modified, skipped, or the like without departing from the scope of the invention.

FIG. 10b is a flow diagram 870 illustrating various operations for visually aligning the subject with the object in the single axis based on the parallax of the object and the parallax of the subject, according to an embodiment as disclosed herein.

At 871, the method includes determining the difference in the apparent position of the subject viewed along the first view point and the second view point based on the movement of the subject in the field of view. In an embodiment, the method allows the parallax controller 225 to determine the difference in the apparent position of the subject viewed along the first view point and the second view point based on the movement of the subject in the field of view.

At 872, the method includes determining the parallax of the first stereo image and the second stereo image of the subject based on the difference in the apparent position of the subject. In an embodiment, the method allows the parallax controller 225 to determine the parallax of the first stereo image and the second stereo image of the subject based on the difference in the apparent position of the subject.

At 873, the method includes visually aligning the subject with the object in a single axis based on the parallax of first and second stereo images of the subject. In an embodiment, the method allows the alignment controller 226 to visually align the subject with the object in a single axis based on the parallax of first and second stereo images of the subject.

The various actions, acts, blocks, steps, or the like in the flow diagram 870 may be performed in the order presented, in a different order or simultaneously. Further, in some embodiments, some of the actions, acts, blocks, steps, or the like may be omitted, added, modified, skipped, or the like without departing from the scope of the invention.

FIGS. 11a-11e are example illustrations in which the smartphone 200 aligns the subject with the object in the single axis, according to an embodiment as disclosed herein.

As shown in the FIG. 11a, consider an example scenario in which the smartphone 200 can be used to visualize the aligned image of the needle 120 and the vein 110 in the display 260 and the portable apparatus 100 is the clip structure. The medical practitioner carries the smartphone 200 in one hand, where the smartphone is kept in parallel to the field of view of the user skin, this results in achieving a uniform depth below the user skin. The clip structure 100 is coupled to the user skin using the fastening band 112. Further, the clip structure 100 having the pair of light source (102a-102b) for illuminating the vein 110 in the field of view. The smartphone 200 includes pair of stereo image sensors (104a-104b) which are placed in proximity to the user skin, can record the first stereo image of the vein 110 from the first point of view 110 using the first stereo image sensor 104a and the second stereo image of the vein 110 from the second point of view using the second stereo image sensor 104b. The recorded image can be transmitted to the head mounted display 200 via the communication interface 230. As shown in the FIG. 11b, the first stereo image of the vein 110 and the second stereo image of the vein 110 are displayed on a first portion and the second portion of the display 260. The vein images displayed on the FIG. 11b are unaligned initially. Further, the medical practitioner can align the first stereo image of the vein 110 to the second stereo image of the vein 110 into the single axis, by sliding the first stereo image of the vein 110 and the second stereo image of the vein 110 as shown in the FIG. 11c.

Let the medical practitioner carries the needle 120 using another hand in the field of view of the vein 110. The pair of stereo image sensors (104a-104b) of the smartphone 200 detects the needle 120 in the field of view. Further the pair of stereo image sensors (104a-104b) record the first stereo image of the needle 120 from the first point of view using the first stereo image sensor 104a and the second stereo image of the needle 120 from the second point of view using the second stereo image sensor 104a. The needle 120 appears double in the stereo image due to the parallax. As shown in the FIG. 11d, the first stereo image of the needle 120 is displayed on the aligned vein image at a left side portion and the second stereo image of the needle 120 is displayed on the aligned vein image at a right side portion of the display 260. Further, the pair of stereo image sensors (104a-104b) detect the movement of the needle 120 towards the aligned vein image for reducing the parallax of the needle as illustrated by arrow marks.

In an embodiment, when the needle 120 is high above skin, the first stereo image of the needle 120 and the second stereo image of the needle 120 are far apart. If the needle 120 is lowered towards the user skin then, the first stereo image of the needle 120 and the second stereo image of the needle 120 comes closer. And if the needle 120 are in exact place of vein 110 then, the, the first stereo image of the needle 120 and the second stereo image of the needle 120 merge and in single axis with the aligned vein image.

The medical practitioner can gently lower/adjust needle 120, until the first stereo image of needle 120 and the second stereo image of needle 120 aligns with the aligned vein image. This alignment can be used to reduce the parallax of the needle, as the stereo images are taken at the different view point. Further, as shown in the FIG. 11e, the first stereo image of the needle 120 and the second stereo image of needle 120 are in single axis with the aligned vein image based on the movement of the needle with respect to the vein. For example, the needle tip is at the same height/level as the blood vessel (pressing on skin). Further, when vein and needle images are aligned into one, the needle 120 can slowly inserted into the vein 110 by the medical practitioner with live camera IR imagery.

FIGS. 12a-12e are example illustrations in which the stereo-visual localization apparatus 200 aligns the subject with the object in the single axis, according to an embodiment as disclosed herein. The stereo-visual localization apparatus 200 is the smartphone 200, and the subject is the needle and the object is the vein.

In conjunction with the FIG. 11a-11e, the smartphone 200 aligns the needle 120 with the vein 110 in the single axis. In an embodiment, the medical practitioner can gently tilt the needle 120 and move the needle 120 towards the vein. As shown in the FIG. 12e, the first stereo image of the needle 120 and the second stereo image of needle 120 are in the single axis with the aligned vein image based on the movement of the needle with respect to the vein.

FIG. 13 is a flow diagram 1300 illustrating various operations for stereo-visual localization of the object, according to an embodiment as disclosed herein. In an embodiment, the object is the micro-organism, and the stereo visual localization apparatus 200 is the head mounted display.

At 1302, the method includes illuminating, by the pair of light source (102a-102b) of the portable apparatus 100, the field of view in which the object is located, wherein the pair of light source (102a-102b) is situated on the pair of support members which longitudinally sits in parallel on the field of view.

At 1304, the method includes recording, by the pair of stereo image sensors of the portable apparatus 100 which is placed over the object, wherein each of the stereo image sensors is situated on each of the support members, configured to record the first stereo image of the object from the first view point and the second stereo image of the object from the second view point in the illuminated field of view.

At 1304, the method includes generating, by the stereo-visual localization apparatus, a stereo-visual user interface displaying the first stereo image of the object in the first portion and the second stereo image of the object in the second portion.

The various actions, acts, blocks, steps, or the like in the flow diagram 1300 may be performed in the order presented, in a different order or simultaneously. Further, in some embodiments, some of the actions, acts, blocks, steps, or the like may be omitted, added, modified, skipped, or the like without departing from the scope of the invention.

FIG. 14b is an example illustration of the stereo-visual localization apparatus for obtaining a micro-photographic image (under any illumination wavelength like NIR, FIR, Ultraviolet, etc.), according to an embodiment as disclosed herein.

Consider a scenario in which the user wants to observe a micro-organism in a sample/specimen. Let the user uses the portable apparatus 100 to view the micro-organism kept on a field of view (e.g., stand). Further, the first stereo image sensor 104a and the second stereo image sensor 104a captures the micro-organism in the field of view, and transmit the first stereo image of the micro-organism and the second stereo image of the micro-organism to the head mounted display 200. Further, the head mounted display 200 displays the first stereo image of the micro-organism and the second stereo image of the micro-organism on the display 260 as shown in the FIG. 14b.

FIG. 15b is an example illustration of the stereo-visual localization apparatus for displaying the ultrasound images, according to an embodiment as disclosed herein.

Consider a scenario in which the medical practitioner wants to obtain an ultrasound image of the patient. The portable device 100 includes a pair of ultrasound probes (1500a-1500b) configured to send an ultrasound signal to the user skin. In an embodiment, ultrasound probes (1500a-1500b) includes the pair of stereo image sensors (104a-104b). The pair of stereo image sensors (104a-104b) can be for example ultrasound crystals, ultrasound piezo-crystals, ultrasound sensor, or the like.

The ultrasound crystals are placed on the two ultrasound probes. Further, the ultrasound crystals can be moved together or separately for scanning the field of view of the patient. In an embodiment, the ultrasound crystals can be located on an underside of the portable device 100. And the ultrasound crystals are located on each of supporting members of the portable device 100.

The ultrasound probes (1500a-1500b) includes pair of stereo image sensors (104a-104b) configured to record the stereo image of the field of view (e.g., patient hand). Further, the first stereo image sensor 104a and the second stereo image sensor 104a captures the field of view, and transmit to the head mounted display 200. Further, the head mounted display 200 displays the scanned portion of the field of view on the display as shown in the FIG. 15b. The medical practitioner can either perform tilting/rotating the ultrasound probes (part of the protocol claims) to bring the ultrasound images closer on the display. An entire ultrasound 3D system as shown in the FIG. 15b, can be used by the surgeon for precise, magnified, stereo-3D based cannulation of the deeply placed large vein as is needed in the critical surgery.

The embodiments disclosed herein can be implemented through at least one software program running on at least one hardware device and performing network management functions to control the elements. The elements shown in the FIGS. 1a through 15b include blocks which can be at least one of a hardware device, or a combination of hardware device and software module.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A method for stereo-visual localization of an object performed by a portable localization device, the method comprising:
    illuminating, by a pair of light sources, a field of view in which the object is located, wherein each of the pair of light sources is situated individually on each of a pair of support members, the pair of support members each sitting in parallel to a longitude of the field of view;
    capturing, by at least one processor, a first stereo image of the object in the illuminated field of view from a first view point by a first stereo image sensor of a pair of stereo image sensors and a second stereo image of the object in the illuminated field of view from a second view point by a second stereo image sensor of the pair of stereo image sensors, wherein each of the stereo image sensors is situated individually on each of the pair of support members;
    detecting, by the at least one processor, a subject placed over the object in the illuminated field of view;
    capturing, by the at least one processor, a third stereo image of the detected subject from the first view point by the first stereo image sensor and a fourth stereo image of the detected subject from the second view point by the second stereo image sensor;
    generating, by the at least one processor, a stereo-visual user interface comprising the first stereo image of the object in a first portion and the second stereo image of the object in a second portion;
    providing the third stereo image of the subject in the first portion and the fourth stereo image of the subject in the second portion of the stereo-visual user interface;
    detecting, by the at least one processor, a movement of the subject to align the subject in the illuminated field of view with the object;
    determining a difference in an apparent position of the object viewed along the first view point and the second view point based on a movement of the object;
    determining a parallax of the object based on the difference in the apparent position of the object viewed along the first view point and the second view point;
    determining a difference in an apparent position of the subject viewed along the first view point and the second view point based on the movement of the subject;
    determining a parallax of the subject based on the difference in the apparent position of the subject viewed along the first view point and the second view point; and
    visually aligning the subject with the object in a single axis to be overlapped based on the parallax of the object and the parallax of the subject in both the first portion and the second portion of the stereo-visual user interface,
    wherein the pair of support members are physically separated from each other,
    wherein each of the pair of light sources is placed on a down portion of the pair of support members, and
    wherein the pair of support members are configured in a shape of a thimble to be worn by a finger, respectively.

2. The method of claim 1, wherein the parallax of the object and the parallax of the subject is zero when the object and the subject are in the single axis.

3. The method of claim 1,
    wherein the object is a buried structure beneath a user skin and the subject is a needle,
    wherein the third stereo image of the subject appears on a left side of the first stereo image of the object in the first portion of the stereo-visual user interface, and the fourth stereo image of the subject appears on a right side of the second stereo image of the object in the second portion of the stereo-visual user interface, and
    wherein the stereo image sensors are one of a stereo-camera device and an ultrasound device.

4. The method of claim 1, wherein capturing a stereo image of the object in the illuminated field of view comprises:
    capturing a first image of the object from the first view point and a second image of the object from the second view point in the illuminated field of view;
    determining pixels corresponding to the object in the first image and pixels corresponding to the object in the second image; and
    capturing the stereo image of the object by combining the pixels corresponding to the object in the first image with the pixels corresponding to the object in the second image.

5. A method for stereo-visual localization of an object performed by a stereo-visual localization apparatus, the method comprising:
    receiving, from a portable apparatus comprising a pair of light sources and a pair of stereo image sensors, a first stereo image of the object in an illuminated field of view from a first view point and a second stereo image of the object in the illuminated field of view from a second view point;

receiving, from the portable apparatus, a third stereo image of a subject from the first view point and a fourth stereo image of the subject from the second view point;

generating a stereo-visual user interface comprising the first stereo image of the object in a first portion and the second stereo image of the object in a second portion;

providing the third stereo image of the subject in the first portion and the fourth stereo image of the subject in the second portion of the stereo-visual user interface;

detecting a movement of the subject to align the subject in the illuminated field of view with the object;

determining a difference in an apparent position of the object viewed along the first view point and the second view point based on a movement of the object;

determining a parallax of the object based on the difference in the apparent position of the object viewed along the first view point and the second view point;

determining a difference in an apparent position of the subject viewed along the first view point and the second view point based on the movement of the subject;

determining a parallax of the subject based on the difference in the apparent position of the subject viewed along the first view point and the second view point; and visually aligning the subject with the object to be overlapped in a single axis based on the parallax of the object and the parallax of the subject in both the first portion and the second portion of the stereo-visual user interface, wherein each of the pair of light sources is situated individually on each of a pair of support members of the portable apparatus, the pair of support members each sitting in parallel to a longitude of the illuminated field of view, wherein each of the stereo image sensors is situated individually on each of the pair of support members, wherein the pair of support members are physically separated from each other, wherein each of the pair of light sources is placed on a down portion of the pair of support members, and wherein the pair of support members are configured in a shape of a thimble to be worn by a finger, respectively.

6. The method of claim 5, wherein the parallax of the object and the parallax of the subject is zero when the object and the subject are in the single axis, wherein the object is a buried structure beneath a user skin and the subject is a needle, and wherein the first stereo image of the subject appears on a left side of the first stereo image of the object in the first portion of the stereo-visual user interface, and the second stereo image of the subject appears on a right side of the second stereo image of the object in the second portion of the stereo-visual user interface.

7. A portable localization device for stereo-visual localization of an object, the portable localization device comprising:

a transceiver; and at least one processor coupled with the transceiver, wherein the at least one processor is configured to:

illuminate, by a pair of light sources, a field of view in which the object is located, wherein each of the pair of light sources is situated individually on each of a pair of support members, the pair of support members each sitting in parallel to a longitude of the field of view, capture a first stereo image of the object in the illuminated field of view from a first view point by a first stereo image sensor of a pair of stereo image sensors and a second stereo image of the object in the illuminated field of view from a second view point by a second stereo image sensor of the pair of stereo image sensors, wherein each of the stereo image sensors is situated individually on each of the pair of support members, detect a subject placed over the object in the illuminated field of view, capture a third stereo image of the detected subject from the first view point by the first stereo image sensor and a fourth stereo image of the detected subject from the second view point by the second stereo image sensor, generate a stereo-visual user interface comprising the first stereo image of the object in a first portion and the second stereo image of the object in a second portion, provide the third stereo image of the subject in the first portion and the fourth stereo image of the subject in the second portion in the stereo-visual user interface, detect a movement of the subject to align the subject in the illuminated field of view with the object, determine a difference in an apparent position of the object viewed along the first view point and the second view point based on a movement of the object, determine a parallax of the object based on the difference in the apparent position of the object viewed along the first view point and the second view point, determine a difference in an apparent position of the subject viewed along the first view point and the second view point based on the movement of the subject, determine a parallax of the subject based on the difference in the apparent position of the subject viewed along the first view point and the second view point, and visually align the subject with the object to be overlapped in a single axis based on the parallax of the object and the parallax of the subject in both the first portion and the second portion of the stereo-visual user interface, wherein the pair of support members are physically separated from each other, wherein each of the pair of light sources is placed on a down portion of the pair of support members, and wherein the pair of support members are configured in a shape of a thimble to be worn by a finger, respectively.

8. The portable localization device of claim 7, wherein the parallax of the object and the parallax of the subject is zero when the object and the subject are in the single axis.

9. The portable localization device of claim 7, wherein the object is a buried structure beneath a user skin and the subject is a needle, wherein the third stereo image of the subject appears on a left side of the first stereo image of the object in the first portion of the stereo-visual user interface, and the fourth stereo image of the subject appears on a right side of the second stereo image of the object in the second portion of the stereo-visual user interface, and wherein the stereo image sensors are one of a stereo-camera device and an ultrasound device.

10. The portable localization device of claim 7, wherein capturing a stereo image of the object in the illuminated field of view comprises:
  capturing a first image of the object from a first view point and a second image of the object from a second view point in the illuminated field of view;
  determining pixels corresponding to the object in the first image and pixels corresponding to the object in the second image; and
  capturing the stereo image of the object by combining the pixels corresponding to the object in the first image with the pixels corresponding to the object in the second image.

11. A stereo-visual localization apparatus for stereo-visual localization of an object, the stereo-visual localization apparatus comprising:
  a transceiver; and
  at least one processor coupled with the transceiver, wherein the at least one processor is configured to:
    receive, from a portable apparatus comprising a pair of light sources and a pair of stereo image sensors, a first stereo image of the object in an illuminated field of view from a first view point and a second stereo image of the object in the illuminated field of view from a second view point,
    receive, from the portable apparatus, a third stereo image of a subject from the first view point and a fourth stereo image of the subject from the second view point,
    generate a stereo-visual user interface comprising the first stereo image of the object in a first portion and the second stereo image of the object in a second portion,
    provide the third stereo image of the subject in the first portion and the fourth stereo image of the subject in the second portion of the stereo-visual user interface,
    detect a movement of the subject to align the subject in the illuminated field of view with the object,
    determine a difference in an apparent position of the object viewed along the first view point and the second view point based on a movement of the object,
    determine a parallax of the object based on the difference in the apparent position of the object viewed along the first view point and the second view point,
    determine a difference in an apparent position of the subject viewed along the first view point and the second view point based on the movement of the subject,
    determine a parallax of the subject based on the difference in the apparent position of the subject viewed along the first view point and the second view point, and
    visually align the subject with the object to be overlapped in a single axis based on the parallax of the object and the parallax of the subject in both the first portion and the second portion of the stereo-visual user interface,
  wherein each of the pair of light sources is situated individually on each of a pair of support members of the portable apparatus, the pair of support members each sitting in parallel to a longitude of the illuminated field of view,
  wherein each of the stereo image sensors is situated individually on each of the pair of support members,
  wherein the pair of support members are physically separated from each other,
  wherein each of the pair of light sources is placed on a down portion of the pair of support members, and
  wherein the pair of support members are configured in a shape of a thimble to be worn by a finger, respectively.

12. The stereo-visual localization apparatus of claim 11, wherein the parallax of the object and the parallax of the subject is zero when the object and the subject are in the single axis,
  wherein the object is a buried structure beneath a user skin and the subject is a needle, and
  wherein the first stereo image of the subject appears on a left side of the first stereo image of the object in the first portion of the stereo-visual user interface, and the second stereo image of the subject appears on a right side of the second stereo image of the object in the second portion of the stereo-visual user interface.

* * * * *